United States Patent
Timms

(10) Patent No.: US 7,122,322 B2
(45) Date of Patent: Oct. 17, 2006

(54) ENDOMETRIOSIS-SPECIFIC SECRETORY PROTEIN

(75) Inventor: Kathy L. Timms, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 10/306,903

(22) Filed: Nov. 27, 2002

(65) Prior Publication Data

US 2003/0166014 A1    Sep. 4, 2003

Related U.S. Application Data

(63) Continuation-in-part of application No. 09/044,604, filed on Mar. 19, 1998, now Pat. No. 6,531,277, which is a continuation-in-part of application No. 08/328,451, filed on Oct. 25, 1994, now abandoned.

(51) Int. Cl.
   *G01N 33/53*   (2006.01)
   *G01N 33/567*  (2006.01)
   *C07K 16/18*   (2006.01)

(52) U.S. Cl. ............... 435/7.1; 435/7.21; 435/40.5; 435/40.52; 435/960; 436/503; 436/87; 530/389.3

(58) Field of Classification Search ............ 435/7.21, 435/9.75, 806, 7.1, 40.5, 42.52; 436/65, 436/87, 814, 966, 510, 514, 503; 530/389.3

See application file for complete search history.

(56) References Cited

OTHER PUBLICATIONS

Nothnick et al., 1994. Detection of a unique 32-kd protein in the peritoneal fluid of women with endometriosis. Fertility and Sterility 61: 288-293.*
Hoffman et al., 1996. A haptoglobin-like glycoprotein is produced by implantation-stage rabbit endometrium. Biology of Reproduction 55: 176-184.*
Dunselman et al., 1988. The acute-phase response in endometriosis of women. J. Reprod. Fert. 83: 803-808.*
Olson et al., 1997. Specific expression of haptoglobin mRNA in implantation-stage rabbit uterine epithelium. Journal of Endocrinology 152: 69-80.*
Boe et al., 1994. Determination of haptoglobin expression in IL-6 treated HepG2 cells by an ELISA and by RNA hybridization—evaluation of a quantitative method to measure IL-6. J. Immunological Methods 171: 157-167.*
Wagner et al., 1996. Haptoglobin phenotyping by newly developed monoclonal antibodies. J. Immunology 156: 1989-1996.*

* cited by examiner

*Primary Examiner*—Christopher L. Chin
*Assistant Examiner*—James L. Grun
(74) *Attorney, Agent, or Firm*—Kohn & Associates, PLLC; Kenneth I. Kohn

(57) ABSTRACT

A method and kit of diagnosing endometriosis in a female patient suspected of having endometriosis. The method includes obtaining a sample from the patient. The sample is analyzed to detect the presence of a purified and isolated endometriotic haptoglobin designated ENDO-I and functional analogs thereof. A therapeutic for treating endometriosis by modulating the expression of a purified and isolated endometriotic haptoglobin designated ENDO-I and functional analogs thereof and a pharmaceutically acceptable carrier.

3 Claims, 4 Drawing Sheets

ENDOMETRIOSIS-SPECIFIC SECRETORY PROTEIN

CROSSREFERENCE TO RELATED APPLICATIONS

This application is a Continuation-In-Part of U.S. Ser. No. 09/044,604, filed Mar. 19, 1998 now U.S Pat. No. 6,531,277, which is a Continuation-In-Part of U.S. Ser. No. 08/328,451, filed Oct. 25, 1994 now abandoned.

GOVERNMENT SUPPORT

The research carried out in connection with this invention was supported in part by a grant from the National Institute of Health, DHHS NICHD R29HD29026. The Government has certain rights in this invention.

BACKGROUND OF THE INVENTION

1. Field of the Invention

The present invention relates to the field of fertility and more particularly, to means and methods for determining and diagnosing endometriosis in women.

2. Description of Related Art

Endometriosis is defined as the ectopic presence of endometrial glands and stroma. Endometriotic tissue is comprised of tissue that is histologically similar yet biochemically and functionally different or out of phase from that of the uterine endometrium.

For example, endometriosis differs from its uterine counterpart in steroid responsiveness and receptor content [Vierikko, et al., 1985; Lessey et al., 1989; Melega et al., 1991] and expression of epidermal growth factor and epidermal growth factor receptor [Melega et al., 1991; Haining et a., 1991]. These altered characteristics, combined with an ectopic location, affect the physiological activity of the endometriotic tissue and thereby alter protein synthesis and secretion by the endometriotic tissue. Deviations in protein synthesis and secretion might be useful in developing unique markers for the nonsurgical diagnosis and management of endometriosis. Unfortunately, limited information is available concerning protein synthesis, secretion, regulation and expression in endometriotic tissue.

Applicant has found dissimilarities in protein synthesis and secretory patterns between eutopic and ectopic uterine tissues (endometriotic implants) using a rat model for endometriosis [Sharpe et al., 1991; Sharpe and Vernon, 1993]. Three endometriosis-associated proteins, synthesized and released in an alternate fashion from uterine proteins, were identified. Two endometriotic proteins named ENDO-I and ENDO-II by applicant ($M_r$ 40,000 to 55,000; pI 4.0 to 5.2 and $M_r$ 30,000 to 32,000; pI 7.0 to 9.0, respectively) were produced by endometriotic implants and not the uteri. The third protein ($M_r$ 70,000; pI 5.7), previously identified in uterine explant cultures as progesterone-induced uterine protein-1 (PUP-1) [Sharpe et al., 1991], appeared in endometriotic implant cultures 24–48 hours later than in uterine cultures [Sharpe and Vernon, 1993]. The identities, functions, mechanisms of altered protein synthesis and secretion by the ectopic uterine tissues and their correlation to the human endometriosis condition were not known at that time.

Little information in the literature addresses human endometriotic secretory proteins. Isaacson and coworkers [Isaacson et al., 1989] showed that human endometriotic tissues produce and secrete complement component 3 (C3) in an alternate fashion to that of the uterine endometrium. Secretion of C3 into the peritoneal cavity may elicit some of the immunological phenomena observed in patients with endometriosis and be related to the pathophysiology of the disease. However, while C3 may play a role in the pathophysiology of endometriosis, C3 is also produced by other tissues in the body and therefore is not useful in the development of an endometriosis-specific marker for the disease.

Further identification of biochemical dissimilarities between the uterine endometrium and endometriosis in vitro may enhance understanding of the mechanism(s) of the pathogenicity of the endometriotic tissue in vivo, potentially leading to the development of improved diagnosis and treatment for endometriosis. Therefore, Applicant desired to identify unique proteins synthesized and secreted by human endometriosis and endometrium in vitro and in vivo for the development of endometriosis-specific markers for diagnosis of the disease. Aberrant production or secretion of proteins by ectopic endometrium in the peritoneal cavity may contribute to the processes of endometriosis, infertility, pelvic adhesive disease and pelvic pain. A specific endometriosis-induced protein could be useful in diagnosis and nonsurgical management of the disease.

SUMMARY OF THE INVENTION

According to the present invention, there is provided a method and kit for diagnosing endometriosis in a female patient suspected of having endometriosis. A sample is obtained from a patient. The sample is analyzed to detect the presence of a purified and isolated endometriotic haptoglobin designated ENDO-I and functional analogs thereof. Also provided is a therapeutic for treating endometriosis by modulating the expression of a purified and isolated endometriotic haptoglobin designated ENDO-I and functional analogs thereof and a pharmaceutically acceptable carrier.

DESCRIPTION OF THE DRAWINGS

Other advantages of the present invention will be readily understood as the same becomes better understood by reference to the following detailed description when considered in connection with the accompanying drawings wherein:

(FIG. 3B) endometrial epithelial cell culture, day 12, cytokeratin mAb (<open arrow>, three-dimensional mound of epithelial cells; <arrowheads>, interconnecting tubular processes; '200); (FIG. 3C) endometrial stromal cell culture, day 8, vimentin mAb ('400); (FIG. 3D) endometriotic epithelial cell culture, day 6, BMA 180/cytokeratin mAbs ('200); (FIG. 3E) endometriotic epithelial cell culture, day 8, cytokeratin mAb ('400); (FIG. 3F) endometriotic stromal cell culture, day 8, vimentin mAb ('400).

DETAILED DESCRIPTION OF THE INVENTION

Figure 1A:
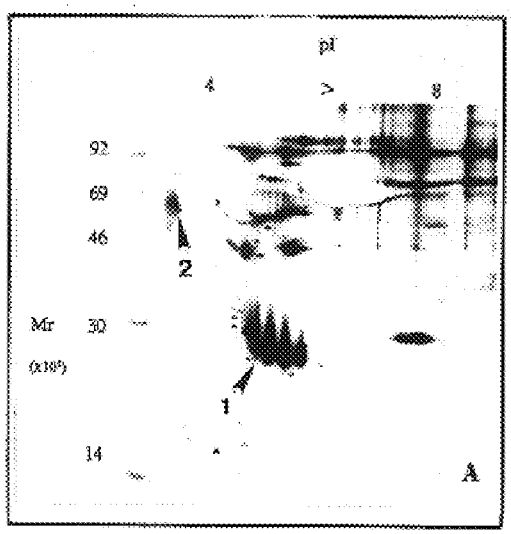
FIG. 1A–1D are representative two-dimensional SDS-PAGE fluorographs of L-[$^{35}$S] methionine-labeled secretory proteins from secretory phase endometrial epithelial cell (FIG. 1A), endometrial stromal cell (FIG. 1B), endometriotic epithelial cell (FIG. 1C), and endometriotic stromal cell (FIG. 1D) culture media.
Figure 1B:
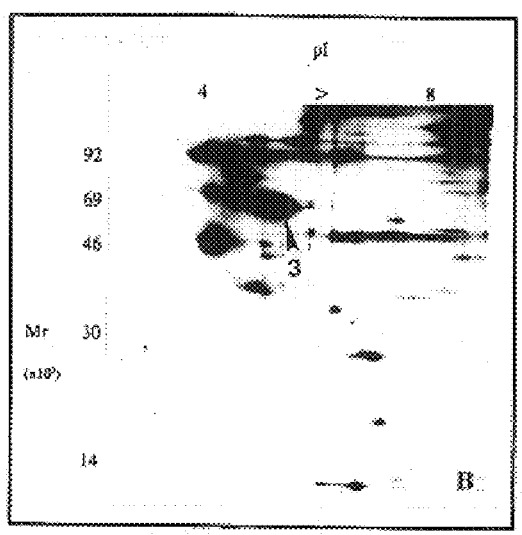

Generally, the present invention provides purified and isolated glycoprotein and biologically functional analogs thereof having specific physical and functional characteristics that characterize the invention over all known prior art for the diagnosis of endometriosis.

The glycoprotein is specifically an N-acetyl linked glycoprotein as determined by in vitro incorporation of D-[6-$^3$H]glucosamine and by binding to wheat germ agglutinin sepharose column (which "sees" certain N-acetylglucosamine and terminal sialic acid residues) [Sharpe et al., 1989, 1991, 1993].

A purified and isolated human glycoprotein named ENDO-I and analogues thereof are disclosed which has a molecular weight of 35,000 to 50,000 Da as determined by two-dimensional SDS-PAGE polyacrylamide gel electrophoresis and an isoelectric point of 4.0 to 5.5. (It should be noted that in some references ENDO-I is referred to as endometriosis protein group I to indicate the glycosylation variants.)

ENDO-I is a secretory protein that is synthesized and secreted by the endometriosis tissue (ectopic endometrial glands and stroma) but not uterine endometrium from women without endometriosis in vitro or in vivo. Reverse transcriptase polymerase chain reaction (RT-PCR) confirmed that ENDO-I transcripts are differentially expressed by endometriosis but not by uterine tissues from women without endometriosis. Human ENDO-I has a cDNA sequence as set forth in SEQ ID No:1.

More specifically, peritoneal endometriotic tissues synthesize and secrete haptoglobin (pHp), which has an analogous nucleotide sequence to hepatic haptoglobin found in serum (sHp). Enzymatic digestions and lectin binding assays were performed to determine differences in protein glycosylation between sHp and pHp, which can provide insight into pHp function and/or identify epitopes for development of methods of medical management of endometriosis. To reduce the dependence on surgical collection of peritoneal tissues from women, recombinant peritoneal Hp (rpHp) was produced and its glycosylation analyzed for future functional studies. These results showed the apparent molecular weight of pHp was 3 kDa smaller than sHp. Desialylation and complete N-deglycosylation elicited similar shifts in sHp and pHp electrophoretic migration, suggesting similar sialic acid content and indicating the 3 kDa variance was due to carbohydrate content, not protein degradation, respectively. Sequential deglycosylation of the four sHp N-glycan chains caused a 3 kDa shift per N-glycan removed suggesting the 3 kDa difference between sHp and pHp can be one N-glycan chain. Lectin ELISA and lectin-blotting analyses demonstrated increased pHp and rpHp interactions with MAL and LTL but no difference in binding to SNL compared to sHp from healthy individuals, identifying variations in the ratios of α(2-3) to α(2-6) sialic acid and fucose residues. Recombinant pHp was 100-fold over-expressed with a similar glycosylation pattern to pHp. The results disclosed herein are the first to identify and establish differences between pHp and sHp glycosylation and specifically characterize anomalies in glycan composition and structure.

The ability to distinguish between the glycosylation differences disclosed above imparts pHp with known immunomodulatory functions that can be used as epitopes in immune-based therapeutics for the non-surgical management of endometriosis. In other words, the present invention also provides therapeutics directed to the haptoglobin of the present invention for the non-surgical treatment of endometriosis in a pharmaceutically acceptable carrier. The therapeutics of the present invention can prevent or at least decrease the secretion or presence of the haptoglobin described above.

Further, the determination of the glycosylation pattern enables a blood test for detecting the presence of the haptoglobin to be performed. The blood test is able to detect the presence of the haptoglobin disclosed herein without confusion with the related hepatic haptoglobin.

Interestingly, human ENDO-I cDNA matches human haptoglobin β-chain with 5 mismatches indicating the ENDO-I may be a member of the haptoglobin superfamily. However, these mismatches provide significant changes in ENDO-I protein configuration folding or glycosylation [Dennis, 1995] providing changes in protein function [Pilotti et al, 1997] as well as unique epitopes for antibody recognition.

Rat ENDO-I has also been isolated and characterized. It has a molecular weight of 35,000 to 55,000 as determined by two-dimensional SDS-PAGE polyacrylamide gel electrophoresis and a cDNA sequence as set forth in SEQ ID No:2 as shown in Example 7. The N-terminal amino acid sequence of rat ENDO-I was also determined as described herein below and is set forth in SEQ ID No:3 (see Example 3).

The term Analogue as used herein is defined as a glycoprotein variant (alternatively the terms amino acid sequence alteration, amino acid sequence variant can be used) with some differences in their amino acid sequences as compared to the native human sequence encoded by the nucleic acid sequence of SEQ ID No:1 but with the same antigenic or biological function. Ordinarily the analogue will be generally at least 70% homologous over any portion that is functionally relevant. In more preferred embodiments the homology will be at least 80% and can approach 95% homology to the glycoprotein. The amino acid sequence of an analog may differ from that of the glycoprotein when at least one residue is deleted, inserted or substituted. Differences in glycosylation can provide analogs. The molecular weight of a glycoprotein can vary between the analog and the present invention due to carbohydrate differences.

Functionally relevant refers to the biological property of the molecule and in this context means an in vivo effector or antigenic function or activity that is directly or indirectly performed by a naturally occurring protein. Effector functions include but are not limited to include receptor binding, any enzymatic activity or enzyme modulatory activity, any carrier binding activity, any hormonal activity, any activity in promoting or inhibiting adhesion of cells to extracellular matrix or cell surface molecules, or any structural role. The antigenic functions essentially mean the possession of an epitope or antigenic site that is capable of cross-reacting with antibodies raised against a naturally occurring endometriosis-associated protein ENDO-I. Biologically active ENDO-I analogues share an effector function of the native ENDO-I, which may, but need not, in addition possess an antigenic function.

The purified and isolated glycoprotein of the present invention can be isolated by methods known in the art such as column chromatography. A specific example of a method is set forth in the Examples herein below. Further the protein of the present invention can be prepared recombinantly from the cDNA sequence as is known in the art.

The present invention further provides a method of diagnosing endometriosis in a female patient suspected of having endometriosis. The method includes the steps of obtaining a sample from the patient and analyzing the sample for the presence of ENDO-I (protein or mRNA) as compared to non-endometriotic controls that do not express ENDO-I.

In an embodiment a fluid sample can be obtained. The fluid sample can be peritoneal fluid or serum, saliva, tears, urine. In the preferred embodiment peritoneal fluid or serum is used. In a further embodiment a uterine tissue sample is used as shown in the Examples. Applicants have unexpectedly found that ENDO-I in addition to being synthesized and secreted specifically by stromal cells of endometriotic tissue origin in patients with endometriosis appears to be aberrantly expressed in the uterine tissue in patients with endometriosis. The uterine endometrial tissue sample can be obtained by standard methods known in the art.

The sample is analyzed to detect the presence of ENDO-I in the sample compared to non-endometriosis controls that do not have the protein present.

The sample is analyzed by methods known in the art. For fluid samples the method can include partial purification of the proteins from the sample by column chromatography. The tissue samples can be assayed for polypeptides/proteins by immunohistochemical and immunocytochemical staining (see generally Stites and Terr, *Basic and Clinical Immunology*, Appleton and Lange, 1994). The fluid samples can be analyzed by immunoassays such as ELISA, RIA, immunoblots, Western blotting, immunoprecipitation, functional assays for angiogenesis and macrophage activation using established cell lines as is known in the art. For endometrial tissue samples, the tissues/cells can be observed immunohistochemically for the presence of ENDO-I protein. Further, mRNA complementary to the target nucleic acid sequence, can be assayed by in situ hybridization, Northern blotting and reverse transcriptase—polymerase chain reaction (RT-PCR). In a further embodiment, the tissue sample can be cultured and the culture media analyzed as with fluid samples (see also Examples).

Generally, a protocol can be used which includes the steps of obtaining either tissue/cell sample or a fluid sample, endometrial sample, or endometrial biopsy from a patient. In some cases this will be done during a laparoscopic examination or D&C. Those skilled in the art will know the proper procedure for obtaining the sample. For example, peritoneal fluid is simply aspirated with a syringe from the peritoneal cavity. The date of the patients last menstrual period and use of any medication are also recorded. Endometriotic tissues and fluids are classified as proliferative (days 4 to 14) or secretory (days 15 to 28) according to the date of their last menstrual period. In the control studies to determine the method of the present invention (see Examples), endometrial dating and the presence of endometriosis was confirmed by histological evaluation of the endometrium. The present invention allows the diagnosis of endometriosis without surgical intervention.

As discussed herein, two-dimensional polyacrylamide gel electrophoresis, as exemplified in the example section below can be used for identification of the protein. Other methods, such as immunoblot analysis, ELISA radioimmunoassay may also be used.

For use in immunoassays, polyclonal and/or monoclonal antibodies may be prepared against ENDO-I. The immunogen may be a synthetic peptide based on the protein sequence data or prepared recombinantly by cloning techniques from the cDNA sequence or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory*

Manual, Cold Spring Harbor Laboratory, Cold Spring Harbor, N.Y., 1988. These antibodies may then be used to identify ENDO-I and ENDO-2 by techniques well known to those skilled in the art including radioimmunoassay, ELISA or Western blot analysis [Joshi et al., 1981, 1982; Catty and Raykundalia, 1989; Hsu, 1981], immunocytochemically. Antibody fragments may also be prepared from the antibodies and include Fab, F(ab')$_2$, and Fv by methods known to those skilled in the art.

For producing polyclonal antibodies a host, such as a rabbit or goat, is immunized with the immunogen, generally with an adjuvant and, if necessary, coupled to a carrier; antibodies to the protein are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen or immunogen fragment, generally a mouse, and isolation of splenic antibody producing cells. These cells are fused to a cell having immortality, such as a myeloma cell, to provide a fused cell hybrid that has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing β-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody or antibody fragment can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W.H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

The present invention further provides a kit for the practice of the method of the invention wherein an immunoassay is used in the identification of ENDO-I. The kit includes antibody directed against human ENDO-I and both positive (containing ENDO-I) and negative (non-endometriotic) control samples. The kit can also contain additionally the reagents to practice the detection means in the various immunoassays and other assays.

The present invention further provides a kit for the practice of the method of the invention wherein the mRNA for ENDO-I is used in the identification of the presence of ENDO-I. As shown in the examples the probe as set forth in SEQ ID No:11 is specific and is provided in the kit that further includes both positive and negative control samples. The kit may also contain additionally the reagents necessary for the methods associated with identification of the mRNA for ENDO-I.

As shown in the Examples there is a distinct difference in the synthesis and release of ENDO-I by human endometriosis and uterine endometrium in culture. Unique, endometriosis-specific secretory proteins are of importance in the development of novel diagnostic, prognostic and therapeutic methods for the management of endometriosis, thereby reducing the need for surgical intervention in the diagnosis and treatment of this disease. Furthermore, understanding biochemical dissimilarities between endometrium and endometriosis will enhance our knowledge of the etiology and/or pathophysiology of the endometriotic tissue potentially leading to new treatment approaches for the disease.

As shown in the Examples, ENDO-I ($M_r$ 40,000 to 55,000; pI 4.0 to 5.2) was synthesized and secreted by endometriotic cultures but not endometrial cultures from women with regular menstrual cycles, it can be the marker for endometriosis. In addition to its presence in all endometriosis explant culture and endometriosis stromal cell culture media from patients who were not receiving treatment for the disease, ENDO-I was also found in half of the endometriosis cultures derived from women who either had received danazol or had undergone a prior hysterectomy for endometriosis. The continued synthesis and secretion of ENDO-I by endometriotic tissues from women who had undergone these therapies may be one possible explanation for treatment failures. The distinct differences in endometriosis and endometrial protein synthesis and secretion observed add to the growing list of biochemical dissimilarities, which exists between these two tissues.

The above discussion provides a factual basis for the use of ENDO-I for the diagnosis of endometriosis. The methods used with and the utility of the present invention can be shown by the following non-limiting examples and accompanying figures.

EXAMPLES

General Methods:

General methods in molecular biology: Standard molecular biology techniques known in the art and not specifically described were generally followed as in Sambrook et al., *Molecular Cloning: A Laboratory Manual*, Cold Springs Harbor Laboratory, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York. Polymerase chain reaction (PCR) was carried out generally as in *PCR Protocols: A Guide To Methods And Applications*, Academic Press, San Diego, Calif. (1990).

General methods in immunology: Standard methods in immunology known in the art and not specifically described were generally followed as in Stites et al.(eds.), Basic and Clinical Immunology (8th Edition), Appleton & Lange, Norwalk, Conn. (1994) and Mishell and Shiigi (eds.), Selected Methods in Cellular Immunology, W. H. Freeman and Co., New York (1980).

*Immunoassays*: Most of the techniques used in performing immunoassays are widely practiced in the art, and most practitioners are familiar with the standard resource materials that describe specific conditions and procedures. However, for convenience, the following paragraph may serve as a guideline.

In general, ELISAs are the preferred immunoassays employed to assess the amount of ENDO-I in a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, New York, 1989.

Delivery of Gene Products/Therapeutics (Compound):

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intrauterine, and intranasal administration, as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques, which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to 10 mg/kg per day.

Specific Methods:

Endometriotic tissues, including red petechia and reddish-brown lesions, were obtained at the time of laparoscopic examination and confirmed by histological evaluation. Endometriotic tissues were classified as proliferative (days 4 to 14) or secretory (days 15 to 28) according to the date of the donor's last menstrual period. Use of medication was also recorded. Additional tissue specimens were transported to the laboratory in saline and dissected free of adnexa.

Endometriotic stromal cells were obtained by enzymatic dissociation and purified by a series of filtrations and sedimentations. Cells were enzymatically dissociated during a one-hour incubation in Dulbecco's Modified Eagle's Medium/Ham's F-12 (DMEM/Ham's F-12) containing 0.5% collagenase, 0.02% deoxyribonuclease and 2% horse serum in a shaking incubator at 37° C. After one hour, the solutions containing the dissociated cells were filtered through an 88 mm nylon mesh filter. The stromal cell fractions that passed through the 88 mm filter were purified by gravity sedimentation and a final filtration through a 38 mm nylon mesh to remove epithelial cells. Cell viability (trypan blue exclusion) and number were evaluated.

Cell fractions were diluted to a density of $1 \times 10^6$ viable cells/mL and were plated in plastic organ culture dishes for a total of $8 \times 10^5$ viable cells in a surface area of 176.25 mm². Cultures were kept in a humidified incubator at 37° C. with 5% $CO_2$. Culture media consisted of DMEM/Ham's F-12 containing 10% heat-inactivated fetal bovine sera for the first six days of culture. By day 8 of culture, the cells had achieved approximately 95% confluence and protein studies were initiated. The media was replaced with serum-free minimal essential medium containing L-[$^{35}$S] methionine (20 mCi/mL) for 24 hours. Incubations were terminated by centrifugation of the media at 3000×RPM for 15 minutes at 4° C. Media containing the de novo synthesized proteins was dialyzed ($M_r$ cut off 6–8000) against 1.0 mM tris, pH 8.2 at 4° C. and lyophilized.

As controls for the isolated stromal cell fractions, endometriotic tissue explants (approximately 100 mg wet weight) were incubated in MEM in the presence of L-[$^{35}$S] methionine (20 mCi/mL). Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-dimensional polyacrylamide gel electrophoresis (2-D SDS-PAGE) was used to evaluate the de novo synthesized radiolabeled endometriotic proteins. Aliquots of lyophilized cell culture and tissue explant media containing $1.5 \times 10^6$ non-dialyzable cpm (6,000 to 8,000 $M_r$ cutoff) were applied to the first dimension isoelectric focusing gels. Molecular weight markers were added to the polyacrylamide (12%) second dimension slab gels. Proteins separated by two-dimensional SDS-PAGE were transferred to nitrocellulose membranes at one amp constant current for one hour and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps.

Example 1

Isolation and Characterization of Glycoprotein

Materials and Methods

Endometrial and Endometriotic Tissue: Human tissues were obtained from randomly selected, informed volunteer patients routinely presenting to the physicians in the Department of Obstetrics and Gynecology at the University of Missouri Medical School as approved by the Institutional Review Board. Patients presented for a variety of routine diagnostic and therapeutic examinations including diagnosis of endometrial function, endometriosis, tubal ligation for sterilization, routine gynecological care and gamete intrafallopian transfer.

Endometrial tissue was obtained using a Pipelle (Unimar, Wilton, Conn.) endometrial suction curette. Endometriotic tissue was obtained at the time of laparoscopic examination. Peritoneal endometriotic implants, including red petechia and reddish-brown lesions, were elevated with biopsy forceps and the area circumscribed by either laser or sharp dissection. Powder-burn implants and cystic ovarian endometriosis were excluded from the study. Vernon and associates have shown [Vernon et. al., 1986] that the metabolic activity of the reddish implants appears to be greatest when compared with the brown or black lesions. Ovarian endometriosis was excluded to eliminate the possibility of "contaminating" ovarian cells in the cell culture experiments. The date of the patient's last menstrual period and use of any medication were also recorded. Endometrial and endometriotic tissues were classified as proliferative (days 4 to 14) or secretory (days 15 to 28) according to the date of their last menstrual period. Endometrial dating and the presence of endometriosis were confirmed by histological evaluation by the Pathology Department at the University of Missouri. Tissue specimens were transported to the laboratory in saline and, using a dissecting microscope, dissected free of adnexa. Epithelial and stromal cell cultures plus tissue explant cultures were processed as described below.

Epithelial and Stromal Cell Isolation And Purification: Epithelial and stromal cells were obtained by enzymatic dissociation and a series of filtrations and sedimentations according to the protocol of Osteen et al. [1989] with modifications described by Sharpe et al. [1992]. Briefly, cells were enzymatically dissociated from endometrial and endometriotic tissues during a 1 hour incubation in phenol-red free Dulbecco's Modified Eagle's Medium/Ham's F-12 (DMEM/Ham's F-12; Sigma Chemical Co., St. Louis, Mo.) containing 0.5% collagenase (*Clostridium histolyticum*, catalogue number 840-70181H), 0.02% deoxyribonuclease (DNase, Sigma Chemical Co., St. Louis, Mo.) and 2% horse serum (Vector Laboratories, Burlingame, Calif.) in a shaking incubator at 37° C. After 1 hour, the solutions containing the dissociated cells were filtered through an 88 mm nylon mesh filter. The stromal cell fractions that passed through the 88 mm filter were further purified by gravity sedimentation and by a final filtration through a 37 mm nylon mesh to remove remaining epithelial cells. Cell viability (0.04% trypan blue exclusion test) and number (Makler Counting Chamber, T. S. Scientific, Perkasie, Pa.) were evaluated in aliquots of the cells.

The epithelial cell fractions retained by the filters in the initial filtration step were subjected to a second enzymatic digestion for 30 to 45 minutes or until cell clumps were dispersed. The dispersed epithelial cell fractions were further purified by gravity sedimentation and selective attachment procedures [Sharpe et al., 1992]. Cell number and viability were evaluated as described for the stromal cell fractions.

Isolation and purification of epithelial and stromal cells yielded an average of $2.1 \times 10^4$ viable epithelial cells and $2.6 \times 10^5$ viable stromal cells per mg of tissue. Both stromal and epithelial cell fractions were diluted to a density of $1 \times 10^6$ viable cells/mL. Stromal cell suspensions (0.8 mL each) were plated in plastic organ culture dishes (Falcon 3037, Falcon Plastics, Oxnard, Calif.) for a total of $8 \times 10^5$ viable cells in a surface area of 176.25 mm$^2$. Epithelial cell suspensions (0.4 mL) were plated in Millicelle CM culture inserts (Millipore, Bedford, Mass.) coated with 0.2 mL of the extracellular matrix Matrigel® (non-diluted; Collaborative Research Inc., Bedford, Mass.) providing a total of $4 \times 10^5$ viable cells in a surface area of 78.50 mm$^2$. Aliquots of the epithelial cell suspensions were also plated on plastic cultureware for immunocytochemical analysis as Matrigel® often created an unacceptable background in the staining process. Other than the elimination of the high background staining, the results of the immunostaining did not vary between the two culture types (matrix vs. plastic).

All cultures were kept in a humidified incubator at 37° C. with 5% $CO_2$. Culture media consisted of phenol-red free DMEM/Ham's F-12 containing 10% heat-inactivated fetal bovine sera (GIBCO/BRL, Grand Island, N.Y.) for the first 6 days of culture. By day 8 of culture, the cells had achieved approximately 95% confluence and protein studies were initiated. The cultures were rinsed 3 times with phosphate buffered saline and the media was replaced with serum-free minimal essential medium (MEM; Gibco/BRL, Grand Island, N.Y.) containing L-[$^{35}$S] methionine (20 mCi/mL; Du Pont New England Nuclear, Boston, Mass.) for 24 hours. Incubations were terminated by centrifugation of the media at 3000×RPM for 15 minutes at 4° C. Media containing the de novo synthesized proteins were dialyzed ($M_r$ cut off 6–8000) against 1.0 mM tris (hydroxymethyl) aminomethane HCl, pH 8.2 at 4° C. and lyophilized.

Cell morphology was assessed and photomicrographed at plating (day 0) and days 4, 6, 8 and 12 at ×100, ×200 and ×400 magnification using a Nikon DiaphonÔ inverted phase contrast microscope (Nikon, Inc., Garden City, N.Y.) with a Hoffman Modulation Contrast System (Modulation Optics, Inc. Greenvale, N.Y.). Cells were evaluated before and after immunostaining and with a hematoxylin counterstain.

A variety of intermediate filament protein, glycoprotein and secretory protein markers were used to assess the various cell types present in the endometrial and endometriotic cell cultures.

Studies were undertaken to identify a marker that would distinguish between endometriotic cells and peritoneal cells. Murine monoclonal antibodies (MAbs) against: cytokeratins 8, 18 and 19 (for epithelial cells; Biodesign clone NCL-5D3; Kennebunkport, Me.); vimentin (for stromal cells; Boehringer Mannheim clone V9; Indianapolis, Ind.); a human epithelial cell marker directed against a 200 kilo-Dalton glycoprotein, BMA 180 (also known as BW 495/36; for endometrial/endometriotic epithelial cells; Behringwerk AG, Marburg, Germany); and for pregnancy-associated endometrial $\alpha_2$-globulin ($\alpha_2$-PEG; $C_6H11$; for secretory phase endometrial epithelial cells) were used to assess the cells at plating and on days 4, 6, 8 and 12. The $\alpha_2$-PEG ($C_6H11$; 1:100) MAb was used as a marker of secretory phase epithelial cell purification and also as an indicator of physiological function in vitro by Western blot analysis of explant culture media separated by 2D-PAGE.

Single and double labeling immunocytochemical techniques were performed using the Vectastain® ABC (avidin: biotin complex peroxidase procedure) and ABC-AP (avidin: biotin complex alkaline phosphatase procedure) Kits (Vector Laboratories) as per manufacturer's instructions. Peroxidase activity was demonstrated by incubation with 3,3'-diaminobenzidine substrate yielding a brown intracellular precipitate that confirmed peroxidase staining. Alkaline phosphatase activity was demonstrated with the Vectastain® Alkaline Phosphatase Substrate Kit I—Vector Red, yielding a pinkish-red stain that confirmed alkaline phosphatase activity. Cells were counterstained with hematoxylin. Cells incubated with phosphate buffered saline substituted in place of primary antibody were included as negative controls in all immunostaining procedures. Using inverted phase contrast microscopy, multiple fields (×200) per cell type were evaluated for the percent of reactive cells.

Tissue Explant Culture: As controls for the isolated epithelial and stromal cell fractions, endometrial and endometriotic tissue explants (approximately 100 mg wet weight) were incubated in MEM in the presence of L-[$^{35}$S] methionine (20 mCi/mL) as previously used by Sharpe et al. [Sharpe et al., 1991] and Sharpe and Vernon [Sharpe and Vernon, 1993]. Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-Dimensional Electrophoresis and Western Blot Analysis: Two-dimensional polyacrylamide gel electrophoresis (2-D SDS-PAGE) was performed as previously employed by Sharpe et al. [1993] and Sharpe and Vernon [1993]. To evaluate the de novo synthesized radiolabeled proteins, aliquots of lyophilized cell culture and tissue explant media containing $1.5 \times 10^6$ non-dialyzable cpm (6,000 to 8,000 $M_r$ cutoff) were applied to the first dimension isoelectric focusing gels. Molecular weight markers (Pharmacia LKB Biotechnology, Inc. Piscataway, N.J.) were added to the polyacrylamide (12%) second dimension slab gels. Proteins separated by two dimensional SDS-PAGE were transferred to nitrocellulose membranes (Schleicher and Schuell, Keene, N.H.) at one amp constant current for one hour using the Hoeffer Transphor® Blot System (Hoeffer Scientific, San Francisco, Calif.) and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps. Due to the overload of protein in some of the two-dimensional SDS-PAGE gels and possible loss of resolution following transfer of the proteins to nitrocellulose prior to autoradiography, only protein groups representing at least 10% of the integrated intensity were evaluated. Quantitative comparisons between patients or between tissue/cell cultures were not made.

Results

Endometrial and Endometriotic Tissue Specimens: Twenty-nine specimens were evaluated (Table 1). Twenty-two of the specimens were obtained from women with histories of regular menses. Seven additional specimens were obtained from women with a typical or absent menstrual cycles. Specimens ranged from 29 mg to over 4 g in weight. Up to 100 mg of tissue was used for explant culture and remaining tissue was enzymatically dissociated for the cell culture experiments.

Protein Synthesis and Secretion:

Patterns of protein synthesis and secretion made from the isolated endometrial and endometriotic epithelial and stromal cell culture media from women with regular menses are shown in FIGS. 1A–1D. Of the hundreds of proteins visualized on the two-dimensional SDS-PAGE fluorographs, five major groups of unique proteins, unique to either endometrial or endometriotic cultures and each representing at least 10% or more of the total integrated intensity of the radioactivity, were resolved and identified.

Figure 1C:
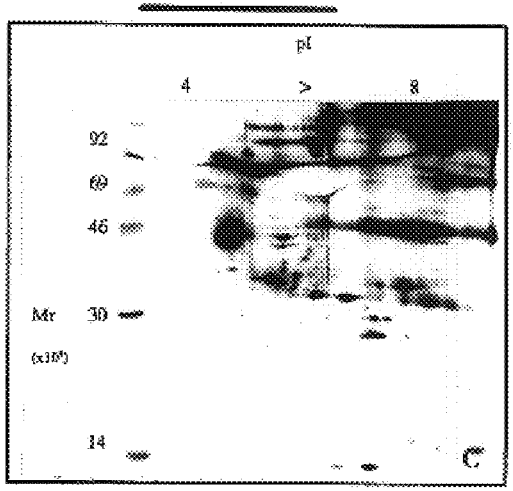
Figure 1D:
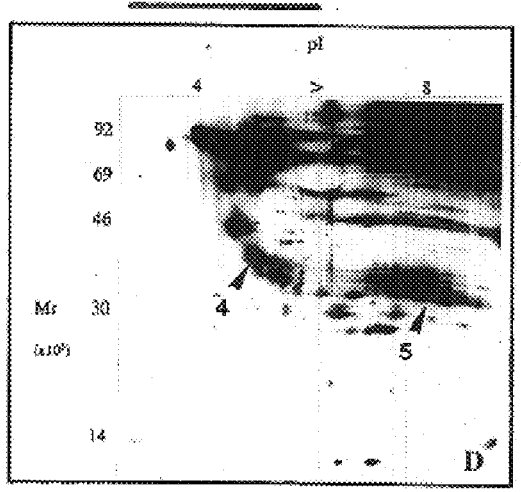

Endometrial Proteins:

Endometrial protein I ($M_r$ 25,000 to 27,000; pI 4.5 to 5.5) and endometrial protein II ($M_r$ 68,000 to 72,000; pI 3.0 to 3.2) were synthesized by secretory, but not proliferative phase, endometrial epithelial cells (FIG. 1A). Endometrial proteins I and II were not found in the culture media of endometrial stromal cells (FIG. 1B), endometriotic epithelial cells (FIG. 1C) or endometriotic stromal cells (FIG. 1D) regardless of the stage of the reproductive cycle. Endometrial protein III ($M_r$ 70,000; pI 5.7) was synthesized and secreted by secretory, but not proliferative phase, endometrial stromal cells. Endometrial protein III was also synthesized and secreted by two of seven proliferative endometriotic specimens (not shown) but none of the secretory phase endometriotic specimens tested (FIGS. 1C and 1D). Thus, the proliferative phase release of endometrial protein III by endometriotic specimens was "out of phase" with that of the secretory phase uterine endometrial release of endometrial protein III.

Endometriotic Proteins:

ENDO-I ($M_r$ 40,000 to 55,000; pI 4.0 to 5.2) and ENDO-II ($M_r$ 30,000 to 32,000; pI 7.0 to 9.0) were produced by endometriotic stromal cells (FIG. 1D) independent of menstrual cycle stage. ENDO-1 and II were not synthesized by endometrial epithelial cells (FIG. 1A), endometrial stromal cells (FIG. 1B) or endometrial epithelial cells (FIG. 1C) regardless of menstrual cycle stage.

Figure 2A:
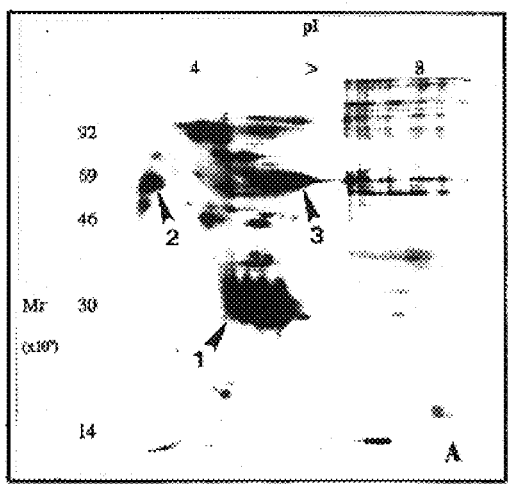
FIG. 2A–2B are representative two dimensional SDS-PAGE fluoragraphs of L-[$^{35}$S] methionine-labeled secretory proteins from secretory phase endometrial epithelial cell (FIG. 2A), and endometriotic (FIG. 2B) explant culture media.
Figure 2B:
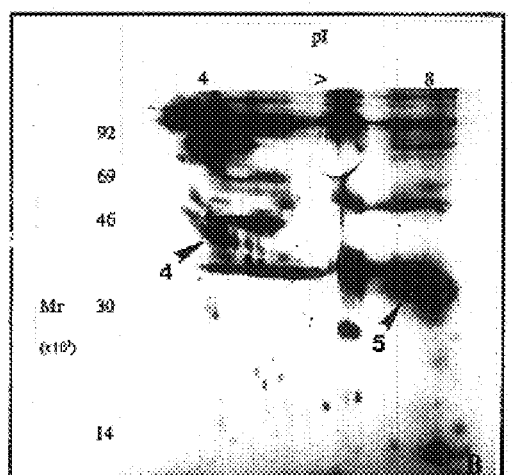

The pattern of ENDO-I synthesis and secretion visualized and evaluated in the cell culture media was identical to that evaluated in the explant culture media (FIG. 2A). Of interest is the finding that ENDO I was not found in endometriotic explant cultures from women with regular menses regardless of the phase of the menstrual cycle (FIG. 2B) while endometrial protein group III was synthesized and secreted by two of seven proliferative phase endometriotic specimens. Also paralleling the cell culture results, ENDO-I was found in endometriotic explant culture media (FIG. 2B) but not endometrial explant culture media (FIG. 2A) regardless of the menstrual cycle stage. Overall, no difference was noted in the pattern of endometrial protein synthesis and secretion between specimens from patients with and without endometriosis.

A limited number of specimens were cultured from women reporting a typical or absent menses. Proliferative endometrium from a patient with irregular uterine bleeding (no current medication) aberrantly synthesized and secreted secretory ENDO-I. This was the only case in which ENDO-I was produced by an endometrial biopsy specimen in this study. Subsequent histological diagnosis revealed adenomyosis also called endometriosis interna).

The pattern of protein synthesis and secretion was also evaluated from endometriotic tissue specimens obtained from patients taking danazol for endometriosis (n=2) and patients who had undergone a prior hysterectomy (n=2). Despite the fact that these women had received therapy for endometriosis, half (n=2/4) of these endometriotic specimens continued to synthesize and secrete ENDO-I.

Figure 3A:
FIG. 3A–3F are photomicrographs of primary cultures of separated epithelial and stromal cells from endometrial and endometriotic biopsy specimens wherein (FIG. 3A) endometrial epithelial cell culture, day 8, cytokeratin mAb ('400)
Figure 3B:
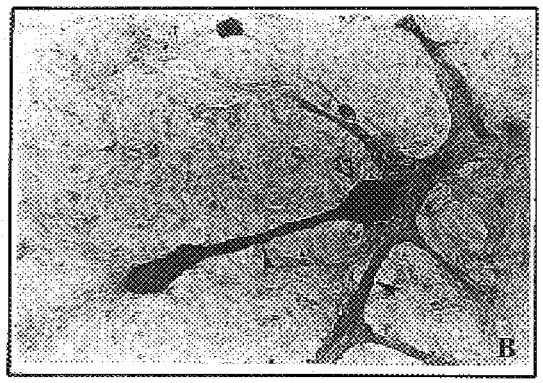
Figure 3C:

Epithelial and Stromal Cell Culture:

Morphologically, by day 8 of culture, endometrial epithelial cells cultured on the extracellular matrices plated on a semipermeable membrane appeared as homogeneous populations of tadpole-shaped cells with prominent, off-centered nuclei and whorling cell-cell processes that wrapped around adjacent cells (FIG. 3A). By day 12 of culture, the monolayers of endometrial epithelial cells formed three-dimensional mounds of cells that appeared interconnected by tubular processes resembling glandular-like structures (FIG. 3B). Endometrial stromal cells displayed a homologous, cobblestone mosaic-like, single cell monolayer pattern. The endometrial stromal cells had centrally located nuclei, distinct cytoplasmic borders that did not overlap and did not demonstrate cell-cell processes throughout the experiment (FIG. 3C).

Figure 3D:
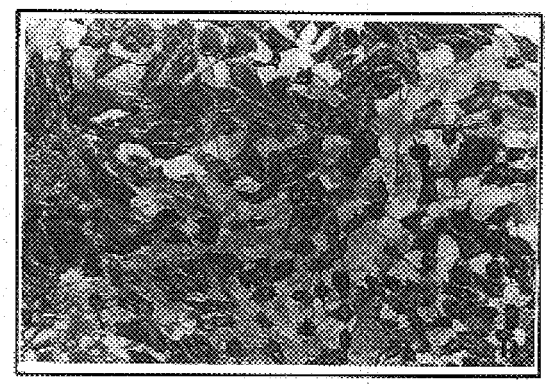
Figure 3E:
Figure 3F:
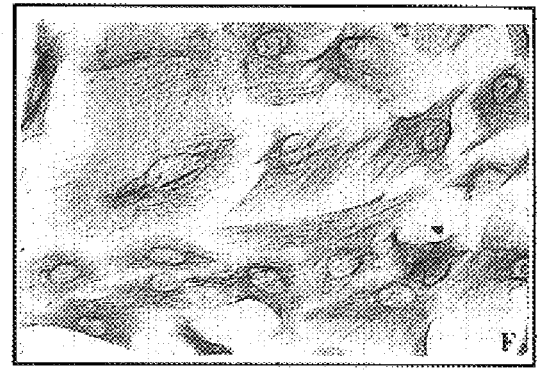

Cell fractions isolated from the endometriotic specimens contained morphologically and immunocytochemically distinct populations of cells. Subconfluent endometriotic epithelial cell fractions observed on days 4 and 6 (FIG. 3D) contained two layers of cells as determined by inverted phase contrast microscopy. An upper layer of cells with multiple long, ultrafine cell-cell processes appeared to be precursors to the tadpole-shaped endometriotic epithelial cells. A sublayer of larger, polymorphous-shaped cells displayed a continuum of cell morphology ranging from polygonal to elongated spindle-like shapes, which were not observed in any of the endometrial epithelial cell cultures. By day 8 of culture (FIG. 3E), the surface layer had overgrown the sublayer so that the cells of the endometriotic epithelial cell cultures appeared tadpole-shaped and morphologically similar to the endometrial epithelial cell cultures (FIG. 3A). The endometriotic stromal cell fractions (FIG. 3F) appeared as single cell monolayers with cells, which had centrally located nuclei, distinct cytoplasmic borders and no obvious cell-cell processes much like the morphology of the endometrial stromal cells (FIG. 3C).

The results of the immunocytochemical staining of the cells did not differ between the day of plating and days 4, 6, 8 and 12 and are presented in Table 2. Endometrial epithelial cells, especially those cells involved in formation of the epithelial cell mounds and tubular gland-like structures, displayed strong immunoreactivity with the cytokeratin and BMA 180 MAbs. Few (<3%) of the cells in the endometrial epithelial cells were decorated with the vimentin MAb suggesting limited stromal cell contamination of the epithelial cell cultures. Secretory, but not proliferative phase, endometrial epithelial cells were also decorated with the $a_2$-PEG MAb (C6H11). The surface layer of tadpole-shaped endometriotic epithelial cells displayed similar immunostaining characteristics to the endometrial epithelial cells for cytokeratin, vimentin and BMA 180, but only the endometrial epithelial cells were decorated with the MAb raised against human $a_2$-PEG (Table 2).

The surface and sublayers of the endometriotic epithelial cell cultures displayed different patterns of immunostaining (Table 2). While both layers stained positively for cytokeratin and negatively for a2-PEG, double antibody staining techniques revealed that only the upper layer of tadpole-shaped cells was decorated with the BMA 180 MAb (FIG. 3D) and only the polymorphous sublayer was decorated with vimentin.

Endometrial and endometriotic stromal cells were both decorated with the vimentin MAb and did not display immunoreactivity with the epithelial cell markers BMA 180 and $a_2$-PEG. However, only the endometriotic stromal cells were decorated with the cytokeratin MAb.

Example 2

The Synthesis and Release of Endometriotic Secretory Proteins Differs from that of the Uterine Endometrium To assess the ability of the endometriotic lesion to synthesize and secrete endometrial proteins, in vitro protein production by uterine endometrium and endometriotic tissues was examined. Matched biopsy specimens of uterine and endometriotic tissues were collected at the time of laparoscopic diagnosis for endometriosis. Menstrual cycle stage (n=5 follicular {cycle day 4–12} and 7 secretory {cycle day 19–27}) and the presence of endometriosis was documented histologically. Tissue explants plus isolated, purified 90% confluent epithelial and stromal cells were cultured for 24 hours in minimal essential medium containing $^{36}$S-methionine (100 mCi/ml). Tissue and cell culture media containing the de novo synthesized proteins was centrifuged, dialyzed and lyophilized and the proteins separated and visualized by two-dimensional gel electrophoresis and fluorography.

Although both tissue types produced hundreds of similar proteins, unique secretory products of the epithelial cells of the secretory uterine endometrium were found that were not secreted by the endometriotic tissue regardless of the cycle day. The two-dimensional electrophoretic mobility and distinctive epithelial cell secretory pattern suggest that one of these is β-lactoglobulin (pregnancy associated endometrial a-globulin, $a_2$-PEG), a major secretory protein of the glandular epithelium of the human endometrium. The second protein is not identified.

A protein was observed that was augmented in stromal cells of the uterine cultures as compared to the endometriotic cultures. This protein co-migrates with the rat progesterone-induced uterine protein-1 (PUP-1, also of stromal origin) and may be the human homologue for PUP-1.

Secretion of a further protein that was identified as ENDO-I (see Example 1) was enhanced in the stromal cells of the endometriotic cultures as compared to those of the uteri.

Example 3

Applicants determined the partial amino acid sequence for the rat ENDO-I glycoprotein as set forth in SEQ ID No: 3. Specifically, rat ENDO-I was given to the Protein Core Facility at the University of Missouri for amino acid sequencing. Partially purified, wheat germ lectin fractionated ENDO-I protein from stromal cell culture media were separated by 2D-PAGE and electrophoretically transferred to polyvinylidene difluoride (PVDF) membranes. A minimum of 50 pmol quantities of protein for amino acid sequencing "off blot" is required. Transfer to PVDF membranes overnight at 4° C. provided samples free of contaminants such as Tris, glycine, sodium dodecyl sulfate or acrylamide. Transferred proteins were visualized by Commassie blue staining and cut from the membrane for sequencing. NH$_2$-terminal sequence analysis was carried out by automated Edman degradation on an Applied Biosystems 470A gas phase sequencer with a Model 120A on-line phenylthiohydantion analyzer.

The partial amino acid sequence for rat ENDO-I is as follows: Ile Ile Gly Gly Ser Met Asp Ala Lys Gly Ser Phe Pro Cys Gln Ala Thr Asn Cys (SEQ ID No: 3).

Example 4

Human cDNA for ENDO-I in Endometriotic Tissue

As shown in the above Examples ENDO-I is synthesized and secreted by rat and human endometriotic explants and endometriotic stromal cells. Further, limited N-terminal sequence analysis (Example 3) showed that rat ENDO-I shares some sequence homology with haptoglobin (Hp).

In this Example the ENDO-I cDNA (see Example 7 for methodology of preparing cDNA) was cloned from human peritoneal endometriosis in order to determine the relative expression of the ENDO-I gene in different human tissues. All tissues were collected at the time of total abdominal hysterectomy. Messenger RNAs (mRNAs) were isolated using the microFast track kit (Invitrogen, CA) and reverse transcribed into the corresponding cDNAs. An adapter primer (AP) that annealed to the polyA tail of all mRNAs was used so that the cDNAs reflected the total mRNA population in the different tissues.

The human RT-PCR primer and the probe for human ENDO-I Southern blot analysis are as follows:

RT-PCR

Forward primer for human ENDO-I 5'-GAT GCC AAA GGC AGC TTT CCC TGG CAG GCT-3'(SEQ ID No:9)

Reverse primer for human: Universal Amplification Primer from GIBCO-BRL 5'-CUA CUA CUA CUA GGC CAC GCG TCG ACT AGT AC-3' (SEQ ID No:10).

Southern Blot

Applicants used a 250 bp DNA fragment that spans from nucleotide 39 to nucleotide 289 of human ENDO-I cDNA.

Sequence of the probe (double stranded DNA)

```
                                           (SEQ ID No:11)
5'-TTCCCACCATAATCTCACCACAGGTGCCACGCTGATCAATGAACAAT

GGCTGCTGACCACGGCTAAAAATCTCTTCCTGAACCATTCACAAAATGCA

ACAGCGAAAGACATTGCCCCTACTTTAACACTCTATGTGGGAAAAAGCA

CCTTGTAGAGATTGAAAAGGTTGTTCTACACCCCAACTACTCCCAGGTAG

ATATTGGGCTCATCAAACTCAAACAGAAGGTGTCTGTTAATGAGAGAGTG

ATG-3'.
```

To clone the ENDO-I cDNA, a polymerase amplification reaction (PCR) was performed using as the template the cDNA population of a human endometriosis sample, a gene specific primer (GSP) based on the Hp sequence and a universal amplification primer that annealed to the AP. To assess the relative expression of the ENDO-I gene in different human tissues, PCRs were carried out with two GSPs based on ENDO-I nucleotide sequence (see Example 7). GAPDH was used as the internal control.

Automated DNA sequence analysis of the peritoneal endometriosis cDNA identified 873 nucleotides that displayed 94.6% and 91% identity with human Hp and Hp-related (Hpr) proteins respectively. The four glycosylation sites at amino acids 23, 46, 50 and 80 of the Hp beta chain were conserved in ENDO-I. Densitometric analysis of ENDO-I gene expression revealed that peritoneal endometriosis produced 100 times more ENDO-I mRNA than endometrium from women without endometriosis. ENDO-I mRNA was undetectable in fallopian tube and in endometrium from women with fibroids.

Example 5

Haptoglobin-related gene product has only been shown to be synthesized by fetal liver. It was therefore unexpected to find some sequence homology with rat ENDO-I N-terminal amino acid sequence as indicated in Example 3.

Using Western Blot, culture media from a human endometriosis explant was examined. A polyclonal antibody raised against human ENDO-I recognizes a single band at approximately 55,000. A monoclonal antibody raised against human haptoglobin did not recognize this band. The anti-haptoglobin antibody stained a large band with a molecular weight less than 50,000. There was no cross-reactivity observed with these antibodies between the proteins. This demonstrates that human ENDO-I and haptoglobin are two distinct proteins.

This was also tested with rat ENDO-I.

Western Blot Analyses: Western blot analyses of 2D SDS-PAGE separations of rat endometriosis explant culture media as describe (12 mg total protein) were performed using rabbit anti-human Hp antibody (1:5000 dilution; DAKO, Carpenteria, Calif.) and mouse anti-human Hp antibody (1:2000 dilution; clone no. HG-36; Sigma Chemical Co., St. Louis, Mo.). Immunostaining was performed using biotinylated anti-rabbit or anti-mouse IgG as secondary antibodies and the Vectastain ABC kit for vinyl membranes as per manufacturer's instructions (Vector Laboratories, Burlingame, Calif.). Peroxidase activity was demonstrated by incubation with 3,3'-diaminobenzidine substrate yielding a brown pigment.

Western Blot Analysis

Western blot analysis using rabbit anti-human Hp antibody was sufficiently sensitive to demonstrate recognition of five to six of the isoforms of ENDO-I protein in 2D SDS-PAGE separations of rat endometriosis explant culture media. Mouse anti-human Hp antibody did not demonstrate immunoreactivity with rat ENDO-I. This demonstrates that rat ENDO-I is also similar but not identical to Hp.

Proteins sharing immunological epitopes with Hp have been reported including pregnancy-associated plasma protein A (PAPP-A), a glycoprotein that increases in concentration in serum through pregnancy [Bueller and Bersinger, 1989; Bischof and Meisser, 1989; Oh et al, 1992]. Further, proteins which share epitopes and antigenicity with Hp and Hpr have been used to diagnose and/or monitor prognosis and therapy in patients with diabetes, Alzheimer's disease and breast and prostate carcinoma among others [Johnson et al, 1992; Kuhadja et al., 1989; Kuhajda et al., 1994; Shurbaji et al., 1992; Dobryszycka, 1992]. Fortunately, Hp exhibits considerable polymorphism that permits distinct diagnosis between these diseases. For example, nine specific Hp a-1 and a-2 variants have been detected in maternal sera of mothers carrying Down syndrome fetuses [Myrick, et al., 1990]. Genetic determination of Hp a subtypes and the calculation of their distribution and allele frequencies have become a significant and useful tool of forensic science for paternity testing and individualization. Assays have also been developed to differentiate between Hp and Hpr in human plasma to allow assessment of Hpr as a clinical marker of malignancy [Oh et al, 1992]. Thus, ENDO-I may represent a unique endometriosis-associated Hp-like protein that can assess the clinical status of endometriosis or as a nonsurgical diagnostic marker for the disease.

Example 6

Interleukin-6 (IL-6) up Regulates Expression of Endometriosis Protein-I (ENDO-I) mRNA As discussed herein, rat and human endometriotic explants and endometriotic stromal cells synthesize and secrete a unique glycoprotein, ENDO-I. Rat and human ENDO-I partial cDNA sequences share significantly identity (>98%) with the b subunit of rat and human haptoglobin (Hp) respectively. Furthermore, ENDO-I mRNA levels are 46-fold greater in pelvic endometriosis than in eutopic endometrium (P=0.024) as determined by semiquantitative RT-PCR, using GAPDH as the internal control. As IL-6 is thought to play an important role in the development of endometriosis and is known to stimulate transcription of haptoglobin mRNA in human liver, the present study was conducted to: (1) study the effects of human recombinant IL-6 on ENDO-I mRNA expression by endometrium from women with endometriosis (UE-E) and by matched samples of pelvic endometriosis (PE) and (2) assess the levels of endogenous IL-6 mRNA in UE-E and PE samples.

ENDO-I mRNA levels were determined by semiquantitative RT-PCR in UE-E and PE samples incubated with and without IL-6. IL-6 transcript levels were determined only in specimens incubated without IL-6. Explants of UE-E and PE were incubated with and without IL-6 (100 ng/ml) in minimal essential medium for 48 hours. Total RNA was isolated and reversed-transcribed into the corresponding cDNAs, using an adapter primer (AP) that annealed to the poly A tail. Polymerase chain reactions (PCRs) were performed to assess the relative expression of ENDO-I, using a gene specific primer (GSP) based on the Hp sequence and a universal adapter primer (UAP) that annealed to the AP sequence. Two GSPs were used to amplify the IL-6 fragment. GAPDH was the internal control. The PCR products were resolved in agarose gels and submitted to Southern blot analysis. The relative amount of ENDO-I and IL-6 transcripts were calculated by dividing the density of each ENDO-I or IL-6 band, respectively, by the density of its corresponding GAPDH fragment. Results between samples incubated with and without IL-6 were analyzed by t-test. Results: IL-6 increased the relative amount of ENDO-I transcript in 29-fold UE-E (P<0.001) and 2-fold in PE as compared to UE-E and PE cultured without IL-6, respectively. IL-6 relative transcript levels were 12-fold greater in PE than UE-E. Significant up-regulation of endometrial ENDO-I expression by IL-6, combined with the increased level of IL-6 transcript in PE versus UE-E indicates ENDO-I expression in vivo by endometriosis is regulated by IL-6 of peritoneal origin.

Example 7

Rat ENDO-I cDNA Isolation

Ribonucleic Acid (RNA) Isolation: For poly A-enriched RNA isolation, rat endometriotic implants, uteri and liver were excised from rats in the estrus and diestrus stages of their estrous cycle as determined by evaluation of vaginal cytology and appearance of the uteri at sacrifice. Tissues were both immediately frozen in liquid nitrogen upon removal from the body and collected following in vitro explant culture, lysed with guanidine isothiocyanate solution (In vitrogen; San Diego, Calif.) and frozen. Poly A-enriched messenger RNA was isolated from the different tissues using the In vitrogen Micro-FastTrack following manufacturer's instructions.

3' Rapid Amplification of cDNA Ends (RACE) and Reverse Transcriptase Polymerase Chain Reaction (RT-PCR): Complementary DNAs were amplified from rat tissues from three different experiments using the SuperScript II Reverse Transcriptase (GIBCO BRL, Gaithersburg, Md.) and the adapter primer from a 3' RACE kit (GIBCO BRL) following the procedure reported by Chenchik et al. [9]. ENDO-I cDNAs were amplified using the 3' RACE procedure in a final volume of 25 ml containing 0.5 ml of cDNA, 20 mM TRIS-HCl (pH 8.4 at 22 C), 50 mM KCl, 1.5 mM $MgCl_2$, 0.2 mM of each dATP, dCTP, dGTP and dTTP, 0.1 mM of universal amplification primer (UAP, GIBCO BRL), 0.1 mM of gene specific primer (GSP):

5'-GACGCCAAAGGCAGCTTICGTTGGGAGGCC-3' (SEQ ID No:4)

corresponding to amino acids 7–16 of ENDO-I and the β-chain of rat Hp [10] and 1.25 U of Taq DNA polymerase (GIBCO BRL). For the 3' RACE of this cDNA a touchdown PCR program was used as follows: 1 min at 94° C. followed by 5 cycles of 94° C. for 30 sec and 72° C. for 5 min; then 5 cycles of 94° C. for 30 sec and 70° C. for 5 min; then 5 cycles of 94° C. and 68° C. for 5 min; followed by a 10-min final extension at 68° C. GAPDH cDNA amplification was performed using similar PCR reagent concentrations. In this case, two GSPs were used: a forward primer:

5'-CCACCCATGGCAAATTCCATGGCA-3' (SEQ ID No:5)

corresponding to nucleotides 152–175 of GAPDH cDNA and a reverse primer:

5'-GCTAAGCAGTTGGTGGTGCAGGA-3' (SEQ ID No:6)

that anneals to nucleotides 451–473 of the GAPDH cDNA. Temperature parameters for this PCR were as follows: 25 cycles at 96° C. for 30 sec, 55° C. for 30 sec and 72° C. for 90 sec with 5 sec autoextension, followed by a 10 min final extension at 72° C.

The ENDO-I and GAPDH PCR products were examined, respectively, on 0.8% and 1.2% agarose/ethidium bromide gels in 1×TBE buffer. A 1 Kb Ladder (GIBCO BRL) was used as a DNA size marker.

Sequence Analysis of the 3' RACE Product: The 950-bp bands amplified from endometriosis and liver samples were electroeluted from agar [12]. First, the purified DNA fragments were sequenced with the fmol DNA Sequencing System (Promega, Madison, Wis.) following the supplier's recommendations. The ENDO-I GSP was end-labeled by polynucleotide kinase with $^{gamma32}$P-CTP (3000 Ci/ml, New England Nuclear, Boston, Mass.) and used as the first sequencing primer. To obtain additional 3' sequence, another GSP:

5-CTCAAGTATGTCATGGTGCC-3' (SEQ ID No:7)

that corresponded to ENDO-I nucleotide sequence 385–404 was designed. A third reverse GSP:

5'-ACTACCTTCTCAATCTCCACCAGC-3' (SEQ ID No:8)

that annealed to nucleotides at positions 186–209 of ENDO-I cDNA was designed to allow us to determine the sequence corresponding to the ENDO-I GSP region. In the last two cases, the sequencing reactions were performed by the University of Missouri DNA Core Facility using Applied Biosystems Prism Dye-Deoxy terminator FS chemistry and analyzed in the Applied Biosystems 377 automated DNA sequencer. The cDNA sequences were compared to known sequences in computerized databanks (Genetics Computer Group, Madison, Wis.).

The ENDO-I PCR fragment amplified from rat endometriosis was sequenced using three GSPs. The analysis shows that ENDO-I cDNA was almost identical to the B-chain of the rat Hp over the 859 bp overlap that corresponds to the coding sequence and the 3' untranslated region of the message. Only one nucleotide was different between ENDO-I and Hp cDNAs, nucleotide 476 of the ENDO-I PCR fragment was a G residue where as this corresponding nucleotide in rat Hp was a C.

Tissue Specific Gene Expression

Using the 3' RACE technique a 950 bp fragment was amplified from sets of rat endometriotic tissue cDNA and in rat liver cDNA (positive control) but not from rat uterus cDNA in three different experiments (see Example 7). This 950 bp fragment comprises coding sequence, 3' untranslated region, the poly A tail, the adapter primer and the universal amplification primer. As an internal control for mRNA/cDNA integrity, an RT-PCR of the housekeeping gene GAPDH was performed. The expected band of 320 base pairs was amplified from all three rat tissues. No difference in expression of the 950 bp transcript was observed between tissues frozen in liquid nitrogen upon excision from the rats or tissues lysed in guanidine isothiocyanate solution and frozen at −80° C. following in vitro explant culture.

Example 8

Endometriosis

Research has shown that established peritoneal endometriotic lesions synthesize and secrete the acute phase response protein haptoglobin (Hp), both in vivo and in vitro (Sharpe, K. L., et al., 1993; Sharpe-Timms, K. L., et al., 1998; Piva, M., et al., 1999; Piva, M., et al., 2001; Sharpe-Timms, K. L., et al., 2000). Further characterization of peritoneal endometriotic Hp (pHp) can provide insight into mechanisms that support known pHp immunomodulatory functions involved in the pathogenesis of endometriosis (Sharpe-Timms K L, et al., 2002) and, by comparing it to hepatic Hp found in the serum Hp (sHp), will help determine the utility of pHp as a novel alternative, non-invasive method for medical management of endometriosis.

Hepatic Haptoglobin

The liver is the most well-known and main site of hepatic Hp production. Hepatic Hp is normally found in the serum (sHp) at concentrations between 1 to 3 mg/ml. Hepatic Hp is a hetero-tetramer consisting of two α-subunits and two-glycosylated β-subunits joined by inter-chain disulfide bonds (Turner G A., 1995). The carbohydrate content of hepatic Hp is ~20% and is found external to the protein, exclusively as N-linked, complex oligosaccharide units called glycans. These occur at four distinct asparagine residues (ASN 23, 46, 50, 80) of each of the β-chains. They can include fucose, galactose, mannose, N-acetyl-glucosamine and sialic acid (Turner G A., 1995; Katnik I, et al., 1994). Hepatic Hp displays heterogeneity in glycosylation. The ratio of α(2-6) to α(2-3) linked sialic acid is about 4:1, the latter are found on the triantennary chains (Nilsson, B., et al., 1981). Approximately 17% of the glycans are mono-sialylated, biantennary glycans. Interestingly, unique and characteristic changes in fucose content, sialic acid content and linkage from α(2-6) to α(2-3) and glycan branching define several diseases, as well as novel modifications in Hp function (Sharpe-Timms K L, et al., 2002; Baseler M W, et al. 1981; Baseler M W, et al., 1983, Oh S K, et al., 1990, Oh S K, et al., 1987, El Ghmati S M, et al., 1996).

Inflammatory cytokines such as interleukin-6 (IL-6) significantly alter glycosylation of acute phase response proteins synthesized by hepatocytes and human hepatoma cell lines, including Hp (van Dijk, W., et al., 1994). These studies have shown that IL-6 modifies glycan branching, but less is known about its effects on terminal carbohydrates (van Dijk, W., et al., 1995). Evidence suggests that inflammation- or disease-induced alterations in terminal fucosylation and sialylation are associated with pathophysiological variations in glycoforms of acute phase response proteins (van Dijk, W., et al., 1994). Moreover, the degree of glycan branching and the type of carbohydrates present on acute phase response proteins depend on the cell type in which they are produced, and profoundly affect the functional properties of the protein (van Dijk, W., et al., 1994).

Endometriosis-Associated Haptoglobin

The nucleotide sequences of sHp and pHp are analogous, both are composed of α- and β-subunits, and the total concentration of Hp in the serum does not vary between women with and without endometriosis, eliminating their potential for diagnostic distinction. Importantly, identification of unique pHp glycan moieties can provide the required specificity and sensitivity to differentiate pHp from sHp for utility as a clinical marker for endometriosis. pHp glycans have not yet been investigated.

In vitro synthesis and secretion of pHp by endometriotic lesion cells and by peritoneal cells is dramatically up-regulated by treatment with IL-6, a cytokine associated with the pathogenesis of endometriosis (Piva, M., et al., 2001). Ectopic endometriotic cells and eutopic endometrial cells from women with endometriosis actually produce significant amounts of IL-6 in vitro as compared to endometrial cells from healthy individuals (Piva, M., et al., 2001). It is possible that, in women with endometriosis, IL-6 production by endometrial and endometriotic cells stimulates expression and alters glycosylation of Hp produced by endometriotic lesions and peritoneal cells.

The most studied biological function of hepatic Hp is the recapture of hemoglobin; yet, Hp has other biological activities distinct from this role. Hp from endometriotic lesions binds to immune cells and alters their function by decreasing their adherence to foreign substrates and increasing IL-6 secretion (Sharpe-Timms K L, et al., 2002). The mechanism of pHp-macrophage interaction has not been defined, but could involve pHp glycosylation and specific integrin receptors present on some immune cells (El Ghmati S M, et al., 1996). As anomalies of immune cell function are believed to be central to the pathogenesis of endometriosis, further characterization of the glycosylation of endometriosis-associated Hp is warranted.

Therefore, to determine if glycosylation differences existed between pHp and sHp, this study performed specific glycosylation analyses by enzymatic digestion and lectin binding assays. Also due to limitations associated with surgical collection of peritoneal tissues in women combined with the need for substantial amounts of correctly glycosylated pHp for future functional studies, a strategy was developed for over-expression of recombinant peritoneal Hp (rpHp) in homologous peritoneal cells transfected with Hp cDNA and the glycosylation of the rpHp product evaluated.

Materials and Methods

*Serum haptoglobin* (sHp)

Blood samples, collected as a source of normal sHp, were obtained by venipuncture from healthy female volunteers (n=5) without pelvic disease as assessed during laparoscopy. These women were non-smokers, non-drinkers and were not taking any hormone-modulating medication. The sera were separated by low speed centrifugation (600×g) and stored at −80° C. Serum Hp from normal individuals was used as the standard to compare pHp glycosylation. Endometriosis-associated endometriotic haptoglobin (pHp)

Endometriotic lesions (n=5) and non-affected serosal peritoneal tissues (n=2) were obtained from subjects with a clinical and histopathological diagnosis of endometriosis as previously described. Cells were obtained from tissues by enzymatic digestion and the adherent cells cultured as previously reported (Piva, M., et al., 2001). Pre-confluent cells were cultured at 37° C. with 5% $CO_2$ in phenol red-free DME/Ham's F12 medium (DME/F12; Sigma) containing 10% heat-inactivated fetal bovine serum (FSB, Life Technologies, Grand Island, N.Y.), 100 IU/ml of penicillin and 100 mg/ml of streptomycin (Sigma). As previously described and validated (Piva, M., et al., 2001), replicate cell cultures were evaluated by cytokeratin (epithelial cell intermediate filament marker, Biodesign, Kennebunk, Me.) and vimentin (stromal cell intermediate filament marker, Roche, Indianapolis, Ind.) immunohistochemical staining.

To enhance Hp expression, near confluent peritoneal cell cultures were cultured with serum-free medium for 48 hours and then exposed to 1 µM DEX (Sigma, St. Louis, Mo.) for 14 hours. Fresh serum-free medium containing 1 µM DEX and 25 ng/ml human recombinant IL-6 (DEX/IL-6) was added every five days for up to one month. As peritoneal endometriotic lesion cells produce high amounts of endogenous IL-6 (Piva, M., et al., 2001) neither DEX nor endogenous IL-6 was added to these cultures.

Cloning of Endometriotic Lesion Hp cDNA and Over-Expression of Recombinant Hp in Primary Peritoneal Cell Cultures Human hepatic Hp is composed of α- and β-subunits translated from the same mRNA, with three different α-chain phenotypes 1-1, 2-1 and 2-2. All three phenotypes are expressed by human peritoneal endometriotic lesions. Full-length endometriotic lesion Hp cDNA was cloned using the Marathon-cDNA Amplification Kit (Clontech, Palo Alto, Calif.). Human peritoneal endometriotic lesion mRNA was reverse-transcribed using the synthesis primer [5'-TTCTA-GAATTCAGCGGCCGC(T)$_{30}$N . . . $_1$N-3'](SEQ ID No: 12). Full-length Hp α$_2$-b and α$_1$-b cDNA were amplified with 0.05 U/µl of Pfu DNA polymerase (Stratagene, La Jolla, Calif.).

The forward primer was:
5'GGGAATTCAGAGGCAAGACCAACCAA-GATGAGTG-3' (EcoR I site) (SEQ ID No: 13).

The reverse primer was:
5'-GTCTAGACTTATCGTCATCGTCGTTCT-CAGCTATG- GTCTTCTG-CCC . . . 3' (Xba I site) (SEQ ID No: 14).

Hp α$_2$-b and α$_1$-β full-length CDNAs were cloned into the mammalian expression vector pcDNA6/V5-HisA (Invitrogen, Carlsbad, Calif.) in the corresponding EcoRI/XbaI sites and sequenced. The final expression construct included a C-terminal tag that encoded for the enterokinase cleavage site DDDK, (SEQ ID No: 15) the V5 epitope GKPIPN- PLLGLDST (SEQ ID No: 16) to monitor expression and a (His)$_6$ metal-binding peptide for affinity-chromatography purification.

Primary cultures of human peritoneal cells were transfected with 10 μg of the recombinant Hp $\alpha_2$-β-pcDNA6N5-His by calcium phosphate methodology following manufacturer's instructions (Invitrogen). Transfected cells were cultured in DME/F12 medium containing FBS, penicillin and streptomycin as described above.

Purification and Quantification of Hp

All culture media were collected every five days and stored separately at −80° C. prior to chromatographic Hp purification. All forms of Hp were chromatographically purified from sera and all cell culture media as previously specified. The purity of all Hp preparations was routinely checked by 10% SDS-PAGE followed by silver staining. A specific Hp ELISA was used to measure Hp concentrations in cell culture media (Piva, M., et al., 2001).

Analysis of Hp Sialic Acid and N-Glycan Content

Sialic acid content of pHp, rpHp and sHp were evaluated by incubating 20 ng of Hp at 37° C. with 10 mIU of *Arthrobacter urefaciens* sialidase (Glyko, Novato, Calif.) in 50 mM sodium phosphate, pH 6.0. This glycosidase releases α (2-3), α(2-6), α(2-8), α(2-9) linked sialic acid from complex carbohydrates. Desialylation efficiency was monitored by lectin blotting analysis with biotinylated *Sambucus nigra* lectin (SNL, Vector Laboratories, Burlingame Calif.), which binds to sialic acid, terminally linked α(2-6) to galactose or N-acetyl galactosamine.

Total N-glycan content of pHp, rpHp and sHp were evaluated by incubating 80 ng of Hp with 2 mIU of recombinant *Flavobacterium meningosepticum* N-glycanase (Glyko), which cleaves intact N-linked glycans from glycoproteins. Additionally, sequential N-glycosylation analyses of sHp were performed by treatment with N-glycanase for 2, 15, 30, 60 minutes and 18 hours. The sequential N-glycosylation analyses of native pHp were not performed, resorting to selective analyses of key glycans, due to limitations of enrolling large numbers of women to undergo invasive surgery as endometriotic tissue donors and the fact that purification of pico- or nanogram quantities of pHp would require peritoneal tissue biopsies from numerous women.

The resultant products of the sHp, pHp and rHp enzymatic reactions were resolved by 10% SDS-PAGE (pHp and sHp) or 8% SDS-PAGE (rpHp), transferred to nitrocellulose membranes (Micro Separations Inc., Westborough, Mass.) and Western blot analyses was performed with rabbit anti-human Hp (Dako, Carpentaria Calif.) as previously described. Apparent molecular weights were calculated by their relative mobility with respect to protein standards.

Lectin ELISA was performed as described by Goodarzi and Turner [31]. *Maackia amurensis* lectin (MAL, Vector Laboratories, recognizes sialic acid terminally linked α(2-3) to galactose or N-acetylgalactosamine), Lotus tetragonolobus lectin (LTL, Sigma, binds fucose linked α(1-2) to galactose, α(1-3) to peripheral N-acetylglucosamine and α(1-6) to the N,N'-diacetylchitobiose core), and SNL were used. MAL, LTL, and SNL were used at concentrations of 10 μg/ml, 2 μg/ml, and 1 μg/ml, respectively. The background absorbance (i.e. without protein) was subtracted from all data. Absorbance was read at 405 nm and the reference wavelength was 630 nm.

Absorbance values at 405 nm (A) MAL, LTL and SNL were plotted against the amount of pHp, rpHp or sHp in ng/100 μl (c) for each independent experiment. The slope (in) for each equation A=mc was calculated using the Excel program (Microsoft Corporation, Redmond, Wash.). These slope values, which represent the amount of lectin bound by one ng of Hp, were normalized by square root transform when necessary (LTL ELISA) and compared by Student's T-test.

Lectin binding was also assessed using the DIG Glycan Differentiation kit from Roche (Indianapolis, Ind.) following manufacturer's instructions. Interactions of Hp and MAL, LTL and SNL were evaluated.

Results

Cell Cultures

Greater than 95% of the peritoneal and endometriotic lesion cells used to produce pHp strongly reacted with the vimentin antibody but not the cytokeratin antibody as previously reported (Piva, M., et al., 2001). Adherent endometrial and peritoneal cell preparations obtained from similar enzymatic digestions and cultured for more than 6 days have been previously characterized to be free of endothelial cells (anti-Factor VIII immuno-negative) and leukocytes (anti-CD 45 immuno-negative) (Sharpe, K. L., et al., 1993). Morphologically, the cells were spindle-shaped and elongated and appeared as a single cell monolayer. A few clusters of polygonal-shaped cells stained for cytokeratin intermediate filaments and were, thus, of epithelial/mesothelial cell origin. These results indicate that the vimentin positive cells used in these experiments consisted basically of cells from mesenchymal origin.

Production of pHp and Cloning and Expression of rpHp

Production of Hp by non-stimulated, non-transfected peritoneal cells (n=2) was below the ELISA detection limit (0.25 ng/ml) (Piva, M., et al., 2001). Endometriotic lesion cells or IL-6 stimulated peritoneal cells (n=7) produced 0.014±0.002 μg of pHp×($10^6$ cells)$^1$×(48 h)$^{-1}$.

Hp α2-b and α1-b cDNAs isolated from human endometriotic lesions were identical to hepatic Hp [35] and contained the signal peptide for secretion and a non-canonical Kozak sequence (AAGATGAG). Transfected peritoneal cells (n=2) secreted 1.4±0.1 μg of rpHp×($10^6$ cells)$^{-1}$×(48 h)$^{-1}$.

Effects of Desialylation and N-Deglycosylation

Three independent experiments performed with pHp from either endometriotic lesion cells or DEX/IL-6 stimulated peritoneal cells showed identical results. Therefore, they will be collectively referred to as pHp throughout the Results Section.

Figure 4:
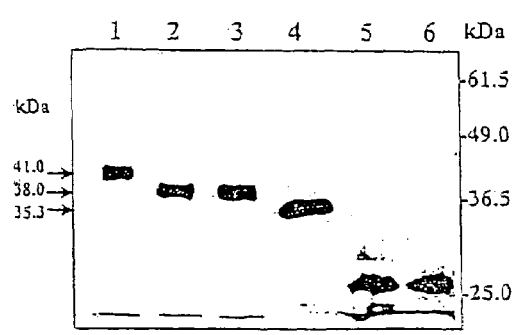
FIG. 4 is a photograph showing the effects of desialylation and N-deglycosylation on electrophoretic mobility of normal sHp and pHp produced under inflammatory conditions; odd-numbered lanes correspond to sHp and even numbered lanes to pHD; proteins were incubated without enzymes (lanes 1 and 2), with sialidase (lanes 3 and 4), or with N-glycanase (lanes 5 and 6); the proteins were resolved by SDS-PAGE, transferred to a membrane and evaluated by Western blot analyses with an antibody to human Hp: at the left of the figure, arrows indicate the apparent molecular weight of non-treated sHp β-subunit (41 kDa), non-treated pHp β-subunit (38 kDa), desialylated sHp (38 kDa) and desialylated pHp (35.3 kDa); protein standards are indicated by their apparent molecular weight at the right of the figure.

FIG. 4 represents the effects of desialylation and N-deglycosylation on the electrophoretic mobility of sHp and pHp as detected by Hp immunoblot analysis. The intact sHp β-subunit appeared as immunoreactive band at 41 kDa whereas the intact pHp β-chain was 3 kDa smaller, with an apparent molecular weight of 38 kDa. Apparent molecular weights of the completely desialylated proteins were calculated as 38 and 35 kDa for sHp and pHp, respectively. Desialylation was complete as treatment of Hp with neuramimidase yielded a product unable to react with SNL as visualized by lectin-blotting analysis.

Complete N-deglycosylation of sHp and pHp with N-glycanase yielded products of equal size (FIG. 4), whose apparent molecular weights (27 kDa) match that of the published amino acid sequence of the deglycosylated sHp β-subunit. No immunoreactivity was detected when an equivalent amount of normal rabbit serum or an equivalent aliquot of an experimental blank were substituted for the Hp antibody and evaluated by anti-Hp Western blot analysis.

Figure 5:
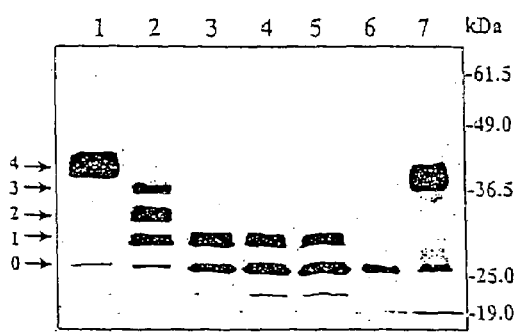
FIG. 5 is a photograph showing the effects of sequential N-deglycosylation and desialylation on electrophoretic mobility of sHp. sHp was incubated without enzymes for 18 hours (lane 1) or with N-glycanase for 2 mm (lane 2), 15 mm (lane 3), 30 mm (lane 4), 60 mm (lane 5) and 18 hours (lanes 6) and sialidase for 18 hours (lane 7); the proteins were resolved by SDS-PAGE, transferred to a membrane and evaluated by Western blot analyses with an antibody to human sHp; at the left of the figure, arrows indicate the number of N-glycan groups per Hp β-chain; protein standards are indicated by their apparent molecular weight at the right of the figure.

Sequential N-deglycosylation of sHp was performed to evaluate shifts in apparent molecular weight that occurred as N-glycans were individually removed from sHp, eventually yielding a completely deglycosylated sHp product (FIG. 5). The untreated sHp β-subunit with all four N-glycans migrated to the anticipated weight at 41 kDa. Partial digestion with N-glycanase over time showed four distinct glycoforms, each approximately 3 kDa smaller than the previous one. Complete N-glycanase digestion resulted in a single form of 27 kDa. These results confirm the work of others showing sHp has four N-linked oligosaccharide units of the complex type (Turner G A., 1995; Nilsson, B., et al., 1981; Katnik I, et al., 1994), each 3 kDa in size. Again, due to limitations in quantities of native pHp available for sequential N-deglycosylation studies, complete structural identification of the native pHp glycans was not performed.

Figure 6:
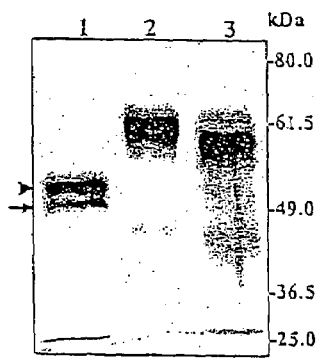
FIG. 6 is a photograph showing the effects of desialylation and N-deglycosylation on electrophoretic mobility of rpHp; after incubating the protein with N-glycanase (lane 1), without enzymes (lane 2) and with sialidase (lane 3), protein mixtures were resolved by SDS-PAGE, transferred to a membrane and evaluated by Western blot analyses with an antibody to human Hp; the arrow and arrowhead indicate a completely and a partially deglycosylated forms of the recombinant protein, respectively; protein standards are indicated by their apparent molecular weight at the right of the figure.

The effects of desialylation and N-deglycosylation on the electrophoretic mobility of rpHp are shown in FIG. 6. The rpHp was secreted into culture medium as a 61-kDa single polypeptide, indicating that the transfected peritoneal cells were unable to cleave the Hp α2-b chain into the two separate subunits. No signal was detected at 38 kDa, as endogenous Hp production by these cells was at least 100 fold lower. Desialylation decreased the apparent molecular weight by about 3 kDa as compared to the non-treated protein. N-glycanase treatment yielded a protein of the expected size at 49 kDa, which is comprised of the 45-kDa Hp α2-b polypeptide and a 4-kDa peptide encoded by the C-terminal tag.

Lectin Analyses

Figure 7A:
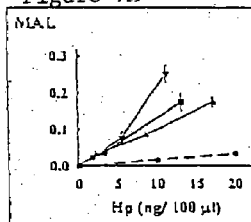
FIGS. 7A through 7C are graphs showing lectin ELISA of pHp produced under the influence of dexamethasone and interleukin-6 (DEX/IL-6; solid lines, three independent experiments represented as ∇, ▲, and ∪) and sHp from healthy individuals (average of five independent experiments, dashed line)
Figure 7B:
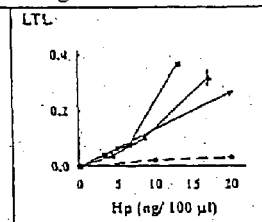
Figure 7C:
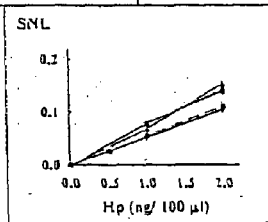

As assessed by lectin ELISA, pHp bound significantly more MAL and LTL compared to sHp from healthy individuals (FIGS. 7A–7C). Binding to SNL was, however, similar for pHp and sHp (FIGS. 7A–7C). More specifically, Hp in each sample was affinity-purified to homogeneity; all values are the means±SEM of duplicate measurements. Significantly more pHp produced under the influence of DEX/IL-6 bound to MAL and LTL in comparison with normal sHp; binding of pHp to MAL and LTL was 10- and 11-times greater, respectively, than sHp ($P<0.001$); no differences were observed between pHp and sHp binding to SNL, suggesting no differences in content of sialic acid terminally linked α2-6 to galactose ($P>0.05$)

Figure 8:
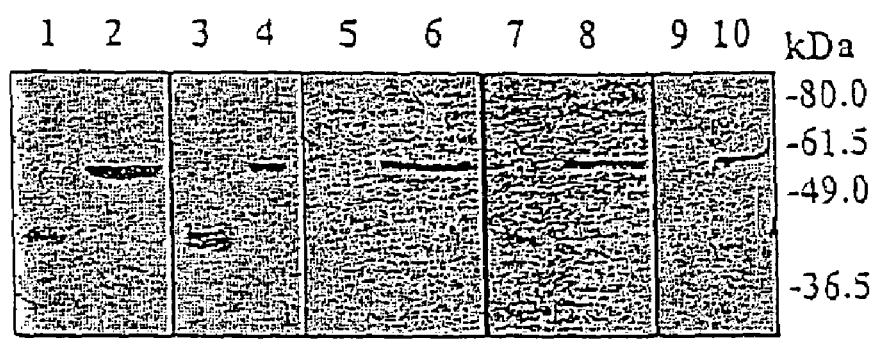
FIG. 8 is a photograph showing lectin-blotting analysis of sHp and rpHp 2-2 expressed in peritoneal cells; sHp is shown in odd-numbered lanes and rpHp is shown in even-numbered lanes; rpHp was secreted as a single $\alpha_2$-β polypeptide and affinity-purified to homogeneity as visualized by silver stained SDS-PAGE (lanes 1 and 2) and Western blot analyses (lanes 3 and 4); lectin-blotting analysis shows that only rpHp stained with MAL (lanes 5 and 6) and LTL (lanes 9 and 10) while both rpHp and sHp reacted with SNL (lanes 7 and 8); Protein standards are indicated by their apparent molecular weight at the right of the figure.
Figure 9A:
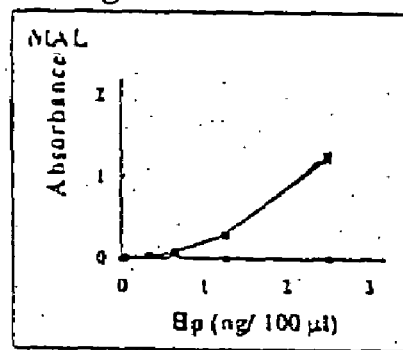
FIGS. 9A and 9B are graphs showing lectin ELISA of rpHp (solid lines, two and three independent experiments for MAL and LTL, respectively, represented by ∇, ▲, and ∪) and sHp from healthy individuals (average of three independent experiments represented by ○), each sample being affinity-purified to homogeneity, all values being the means±SEM of duplicate measurements.
Figure 9B:
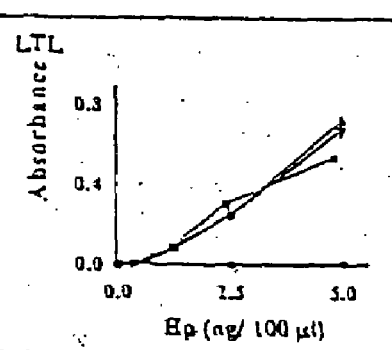

Lectin-blotting analysis comparing binding of rpHp and sHp showed that; like pHp, only rpHp reacted with MAL and LTL, while both sHp and rpHp reacted with SNL (FIG. 8). This result was confirmed by lectin ELISA, where rpHp bound significantly more MAL and LTL than sHp (FIGS. 9A–9B).

Discussion

These results report the discovery and initial characterization of differences in endometriosis-associated Hp protein glycosylation versus hepatic Hp glycosylation. This information provides insight into pHp glycosylation that can be involved in the mechanisms of pHp immunomodulation in the pathogenesis of endometriosis and identifies the presence of pHp glycosylation epitopes that can be used in development of novel, non-invasive immuno-diagnostics or therapeutics for endometriosis.

Under these experimental conditions designed to mimic an inflammatory response (van Dijk, W., et al., 1995), the pHp β-chain was 3 kDa smaller than the sHp β-chain. Several explanations can account for the observed 3 kDa difference between pHp and sHp. Equivalent changes in SDS-PAGE electrophoretic migration of pHp and sHp after desialylation indirectly suggest the sialic acid content of these two glycoproteins is similar. Complete N-deglycosylation proves that the 3 kDa difference between pHp and sHp was in carbohydrate content and not due to protein degradation. The sequential deglycosylation of sHp implies that pHp lacks a complete 3 kDa N-glycan unit an alteration reported in sHp isolated from patients with carbohydrate-deficient glycoprotein syndrome type I.

The lectin binding studies provide further insight into the glycan profiles of pHp and rpHp. The increased interactions of pHp and rpHp with MAL provide evidence of an increase in α(2-3) linked sialic acid residues in these two glycoproteins as compared to the normal 4:1 ratio of α(2-6) to α(2-3) linked sialic acid of sHp [37, 38]. These changes are likely to occur on triantennary chains because α(2-3)-sialyltransferase shows a much higher affinity than α(2-6)-sialyltransferase for oligosaccharides that are part of branched lactosaminoglycan extensions, suggesting pHp and rpHp can have more triantennary glycan chains that sHp. Interestingly, the glycan structure of pHp resembles that of sHp isolated from ovarian cancer patients in which biantennary chains ending in α(2-6) sialic acid are replaced by triantennary chains with terminal α(2-3) sialic acid residues.

The increased binding of pHp and rpHp to LTL suggests differential fucose content or linkages in pHp and rpHp compare to sHp. sHp isolated from breast and ovarian cancer patients also shows a dramatic increase in LTL reactivity without any change in SNL binding or sialic acid content.

In vivo, several factors affect the glycosylation of serum acute phase response proteins including the particular physiological state of the individual (acute inflammation, pregnancy) and the type of disease (cancer, alcoholic liver cirrhosis) (van Dijk, W., et al., 1994). The glycosylation pattern also depends on the acute phase response protein itself. For example, in women with ovarian cancer, serum $\alpha_1$-protease inhibitor exhibits decreased branching and more glycan chains ending in α(2-6) sialic acid while sHp displays increased branching and more glycan chains ending in α(2-3) sialic acid.

Serum Hp from women with endometriosis was not evaluated in these experiments. It is known that serum concentrations of sHp do not differ between women with and without endometriosis, but the glycosylation pattern of sHp from women with endometriosis requires further characterization. Production of pHp by either peritoneal or endometriotic cells is a local effect in the peritoneal cavity, triggered by IL-6 secreted by endometrial cells and/or macrophages. Glycosylation of sHp from the liver would be altered in these women, as it is in association with some other systemic disorders, but further investigation is required.

Others have found no difference in the concentrations of several of the acute phase response proteins, including Hp, in peritoneal fluid of women with endometriosis (Sharpe-Timms K L, et al., 2002), however, the glycosylation of these proteins has not been defined in endometriosis. Peritoneal fluid from women with endometriosis contains numerous inflammatory cytokines, some of which are produced by the endometriotic lesions including IL-6 that could alter the glycosylation of pHp. Further, endometriotic lesions are composed of endometrial and peritoneal cells plus resident immune cells and endothelial cells. Possible interactions with the cells or their products the intact endometriotic lesion can also alter the glycosylation of endometriotic Hp.

In vitro, the cell type (i.e. hepatoma cell line versus hepatocytes) and the cytokine that induces the acute phase response protein are major contributory factors to glycan structure (van Dijk, W., et al., 1994). Studies of primary cultures of hepatocytes have clearly shown that these cells produce all the Hp glycosylation variants present in normal and patient sera. Yet in endometriosis, peritoneal cells only produce pHp when exposed DEX/IL-6 and this pHp is differentially glycosylated as compared to sHp produced by liver cells. As previously mentioned, the fact that IL-6 is known to modify glycan branching (van Dijk, W., et al., 1995) supports the evidence that IL-6 stimulated pHp can have more triantennary N-glycan chains than sHp.

The over-expression strategy using transfected primary cultures of peritoneal cells was successful in producing 100 fold more rpHp than production of pHp by DEX/IL-6 treated peritoneal cells. In support of this model, the host peritoneal cells had a homologous genetic background with the peritoneal component of endometriotic lesion cells. They produced the a typical glycosylation pattern of pHp, deemed to have alterations in the N-glycan chains with more terminal $\alpha(2,3)$-linked sialic acid and core fucose as compared to sHp, and both displayed increased binding to MAL and LTL.

This approach should, however, be used with caution. The fact that the single $\alpha$-b polypeptide rpHp is not processed into the separate $\alpha$- and $\beta$-subunits, possibly due to saturation of specific intracellular protease(s) involved in the Hp maturation process, raises the concern that the glycosylation mechanisms can also be affected in this system. Others have shown that the transfection process or mutations can activate latent glycosyltransferases. Curiously, the glycosylation profiles of pHp produced in DEX/IL-6 treated peritoneal cells and of rpHp produced in peritoneal cells transfected with the Hp gene but without DEX/IL-6 treatment were similar. Further experiments are needed to evaluate the relationship of DEX/IL-6 treatment and glycosyltransferase production associated with transfection and their effects on the overall glycosylation profile of pHp and rpHp. Additionally, it must be determined if over-expressed rpHp from peritoneal cells reflects the same pathophysiological mechanisms and functional status of pHp produced by endometriosis-associated mesenchymal cells.

Collectively, prior research (Sharpe, K. L., et al., 1993; Sharpe-Timms, K. L., et al., 1998; Piva, M., et al., 1999; Piva, M., et al., 2001; Sharpe-Timms, K. L., et al., 2000; Sharpe-Timms K L, et al., 2002) and the present study indicate that like sHp, the pHp glycosylation profile includes biantennary and triantennary chains containing fucose, galactose, mannose, N-acetylglucosamine and sialic acid; however, modifications in the sialic acid linkages and glycan branching and fucose residues exist. As others have shown that these glycans can serve as ligands for immune cell $\alpha$Mb2 integrin receptors (also called CD11b/CD18 and MAC-1) (El Ghmati S M, et al., 1996), the pHp glycosylation modifications are involved in the mechanism whereby endometriotic Hp binds to macrophages. The binding of endometriotic Hp to macrophages alters macrophage function by decreasing their adherence to foreign substrates and increasing IL-6 and TNF-$\alpha$ (Sharpe-Timms, unpublished observation) secretion and in turn increases endometriotic tissue endometriotic Hp production (Sharpe-Timms K L, et al., 2002). Activation of the $\alpha$M$\beta$2 integrin receptor by ligands other than Hp both markedly alters macrophage phagocytic function and enhances production IL-1, IL-6 and TNF-$\alpha$.

In conclusion, the discovery of differential glycosylation pHp, whose production by cells from the peritoneal cavity is up-regulated by IL-6, meets the goals of this study and provides the groundwork for further studies of this extrahepatic Hp in the pathogenesis of endometriosis. Further, recognition of differential glycosylation of pHp compared to sHp suggests novel epitopes exist that could be used to raise specific monoclonal antibodies, essential tools to detect different glycoforms and eventually develop non-invasive diagnostics and pursue immunotherapeutic approaches for endometriosis. And while further studies to provide a complete analysis of pHp sugar composition are warranted, efforts to purify enough pHp to perform these studies must address the ethical concerns of performing significant numbers of invasive surgeries in women to collect endometriotic tissue. At present, while providing a convenient source of abundant protein possessing the same glycosylation profile of pHp, the utility of rpHp for functional studies in the pathogenesis of endometriosis remains to be defined.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains. The entire disclosure of the prior application, U.S. Ser. No. 08/328,451, filed Oct. 25, 1994, and assigned to the same assignee, is hereby incorporated in its entirety by reference into this application.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

TABLE 1

| Source of Tissue Specimens | |
|---|---|
| Tissue Source | No. of specimens |
| Regular menses | |
| Matched endometrial/endometriosis biopsy | 16 |
| Endometrial biopsy only | 2 |
| Endometriosis biopsy only | 4 |
| Total | 22 |
| Atypical of absent menses | |
| Endometrial biopsy, irregular bleeding | 1 |
| Endometrial biopsy, irregular bleeding-MPA | 1 |
| Endometrial biopsy, perimenopausal | 1 |
| Endometriosis biopsy, danazol | 2 |
| Endometriosis biopsy, prior hysterectomy | 2 |
| Total | 7 |

TABLE 2

Immunocytochemical Staining of Isolated Populations of Endometrial and Endometriotic Epithelial and Stromal Cell Fractions

| | Epithelial cell fraction | | | Stromal cell fraction | |
|---|---|---|---|---|---|
| | Endometrial tissue | Endometriotic tissue | | Endometrial tissue | Endometriotic tissue |
| | Tadpole | Tadpole | Polymorph | Cobblestone | Cobblestone |
| Cytokeratin | +* | + | + | o | + |
| Vimentin | o† | o | + | + | + |
| BMA 180 | + | + | o | o | o |
| $\alpha_2$-PEG | s‡ | o | o | o | o |

*+, Immunoreactivity detected during proliferative and secretory phases of the menstrual cycle.
†o, no immunoreactivity detected in either phase of the menstrual cycle.
‡s, immunoreactivity detected only in secretory phase of the menstrual cycle.

REFERENCES

Bischof and Meisser, 1989. Immunological heterogeneity of pregnancy-associated protein-A (PAPP-A). Effects on the radioimmunoassay of PAPP-A. Br J Obstet Gynaec 96:870–5.

Bueller and Bersinger, 1989. Antisera to pregnancy-associated plasma protein-A (PAPP-A) recognizes human haptoglobin. Br J Obstet Gynaec 96:867–9.

Catty and Raykundalia, 1989. ELISA and related enzyme immunoassays. In:Catty D (ed) Antibodies, a practical approach. IRL Press, Oxford. Vol II pp97–154.

Dennis, 1995. A review of the biological significance of carbohydrates on glycoproteins and methods for their analysis. Adv Exp Med Biol 376:1–11.

Dobryszycka, 1992. Relevance of haptoglobin in clinical medicine. Folia Histochemica et Cytobiologica 30:197–200.

Fodor et al, 1993. "Multiplexed biochemical assays with biological chips", Nature 364:555–556.

Haining et al. 1991. Epidermal growth factor in human endometrium: proliferative effects in culture and immunocytochemical localization in normal and endometriotic tissues. Hum Reprod 6:1200–5.

Hillam et al., 1974. Local antibody production against the murine toxin of Yersinia pestis in a golf ball-induced granuloma. Infect Immun 10:458–463.

Hsu et al. 1981. Use of avidin-biotin-peroxidase comples (ABC) in immunoperoxidase techniques: a comparison between ABC and unlabeled antibody (PAP) procedures. J Histochem Cytochem 29:577–580.

Huston et al, 1991. "Protein engineering of single-chain Fv analogs and fusion proteins" in Methods in Enzymology (J J Langone, ed.; Academic Press, New York, N.Y.) 203:46–88.

Isaacson et al., 1989. Production and secretion of complement component 3 by endometriotic tissue. J Clin Endocrin Metab 69:1003–9.

Johnson and Bird, 1991. "Construction of single-chain Fvb derivatives of monoclonal antibodies and their production in Escherichia coli in Methods in Enzymology (J J Langone, ed.; Academic Press, New York, N.Y.) 203: 88–99.

Johnson et al, 1992. Cerebrospinal fluid protein variations in common to Alzheimer's disease and schizophrenia. Applied and Theoretical Electrophoresis 3:46–53.

Joshi et al., 1981. Radioimmunoassay for a progestagen-associated protein of the human endometrium. J Clin Endo Metab 52:1185–1192.

Kawasaki E S. Amplification of RNA. In: PCR protocols: A Guide to Methods and Applications, Innis M A, Gelfand D H, Sninsky J J, White T J, eds. Academic Press, 1990, pp 21–27.

Kuhadja et al., 1989. Haptoglobin-related protein (Hpr) epitopes in breast cancer as a predictor of recurrence of the disease. N Engl J Med 321:636–41.

Kuhajda et al., 1994. Fatty acid synthesis: a potential selective target for antineoplastic therapy. Proc Natl Acad Sci, USA 91:6379–83.

Knudsen, 1985. Proteins transferred to nitrocellulose as immunogens. Anal Biochem 147:285–288.

Lessey et al., 1989. Immunohistochemical analysis of estrogen and progesterone receptors in endometriosis: comparison with normal endometrium during the menstrual cycle and the effect of medical therapy. Fertil Steril 51:409–15.

Melega et al., 1991. Tissue factors influencing growth and maintenance of endometriosis. Ann NY Acad. Sci. 622: 257–65.

Mernaugh and Mernaugh, 1995. "An overview of phage-displayed recombinant antibodies" in Molecular Methods In Plant Pathology (R P Singh and U S Singh, eds.; CRC Press Inc., Boca Raton, Fla.) pp. 359–365.

Myrick, et al., 1990. Identification of haptoglobin alpha-2FF variants in mid-trimester maternal serum as potential markers for Down syndrome. Applied and Theoretical Electrophoresis 1:233–41.

Oh et al, 1992. Quantitative differentiation of the haptoglobin-related gene product from haptoglobin in human plasma: a possible test of tumor-associated antigen. Hybridoma 11:1–12.

Osteen et al., 1989. Development of a method to isolate and culture highly purified populations of stromal and epithelial cells from human endometrial biopsy specimens. Fertil Steril 52:965–72.

Pilotti et al., 1997. Insular carcinoma: a distinct de novo entity among follicular carcinomas of the thyroid gland. Am J Surg Pathol 21 (12):1466–73.

Sharpe, et al., 1991. Detection of a progesterone-induced secretory protein synthesized by the uteri but not the endometriotic implants of rats with induced endometriosis. Fertil Steril 55:403–10.

Sharpe et al., 1992. Proliferative and morphogenic changes induced by the coculture of rat uterine and peritoneal cells: a cell culture model for endometriosis. Fertil Steril 58:1220–9.

Sharpe and Vernon, 1993. Polypeptides synthesized and released by rat endometriotic tissue differ from those of the uterine endometrium in culture. Biol Reprod. 48:1334–1340.

Sharpe et al., 1993. Polypeptides synthesized and released by human endometriosis tissue differ from those of the uterine endometrium in cell and tissue explant culture. Fertil Steril 60:839–51.

Shurbaji et al., 1992. Expression of oncogenic antigen 519 (OA-519) in prostate cancer is a potential prognostic indicator. Am J Clin Path 1992; 97:686–91.

Vernon et al., 1986. Classification of endometriotic implants by morphologic appearance and capacity to synthesize prostaglandin F. Fertil Steril 45:801–806.

Vierikko et al., 1985. Steroidal regulation of endometriosis tissue: lack of induction of 17B-hydroxysteroid dehydrogenase activity by progesterone, medroxyprogesterone acetate, or danazol. Fertil Steril 1985; 43:218–224.

Weibel, 1979. Stereological Methods. In: Practical Methods for Biological Morphometry, Vol 1, New York: Academic Press pgs. 33–45.

Sampson, J. A. Peritoneal endometriosis due to menstrual dissemination of endometrial tissue into the peritoneal cavity Am. J. Obstet. Gynecol. 14, 422–469 (1927).

Nissole, M., and Donnez, J. Peritoneal endometriosis, ovarian endometriosis, and adenomyotic nodules of the rectovaginal septum are three different entities. Fertil. Steril. 68, 585–598 (1997).

Cirkel, U., Ochs, U., Mues B., Zwadlo G., Sorg C., and Schneider, H. P. Inflammatory reaction in endometriotic tissue: an immunohistochemical study, Eur. J. Obstet. Gynecol. Reprod. Biol. 48, 43–50 (1993).

Brosens, I. A. Endometriosis. Current issues in diagnosis and medical management. J. Reprod. Med. 43, 281–286 (1998).

Sharpe, K. L., Zimmer, R. L., Griffin, W. T., and Penney, L. L. Polypeptides synthesized and released by human endometriosis differ from those of the uterine endometrium in cell and tissue explant culture. Fertil. Steril. 60, 839–5 1 (1993).

Sharpe-Timms, K. L., Piva M., Ricke, E. A., Surewicz, K., Zhang Y. L., and Zimmer R. L. Endometriotic lesions synthesize and secrete a haptoglobin-like protein. Biol. Reprod. 58, 988–994 (1998).

Piva, M., Sharpe-Timms K. L. Peritoneal endometriotic lesions differentially express a haptoglobin-like gene. Mol. Hum. Reprod. 5, 71–78 (1999).

Piva, M., Horowitz, G. M., Sharpe-Timms K. L. Interleukin-6 differentially stimulates haptoglobin production by peritoneal and endometriotic cells in vitro: a model for endometrial-peritoneal interaction in endometriosis. J. Clin. Endocrinol. Metab. 86, 2553–2561 (2001).

Sharpe-Timms, K. L., Ricke, E. A., Piva, M., and Horowitz G. M. Differential in vivo-expression and localization of endometriosis protein-I (ENDO-I), a haptoglobin homologue, in endometriuin and endometriotic lesions. Hum. Reprod. 15, 2180–2185 (2000).

Sharpe-Timms K L, Ziminer R L, Ricke E A, Piva M A, Horowitz G M. Endoinetriotic haptoglobin binds peritoneal macrophages and alters their function in endometnosis. Fertil. Steril. 78:810–819 (2002).

Turner G A. Uaptoglobin. A potential reporter molecule for glycosylation changes in disease. Adv. Exp. Med. Blot 376, 231–8 (1995).

Nilsson, B., Lowe, M., Osada J., Ashwell, G., Zopf, D. The carbohydrate structure of human haptoglobin 1–1, in: I. Yamakawa, T. Osawa, S. Uanda, (Eds.), Glycoconjugates Proceedings of the 6th International Symposium on Glycoconjugates, Japan Scientific Societies Press, Tokyo, pp. 275–276 (1981).

Katnik I, Jadach J, Krotkiewski U, Gerber J. Investigating the glycosylation of normal and ovarian cancer haptoglobins using digoxigenin-labeled lectins. Glycosyl. Dis. 1, 97–104 (1994).

Baseler M W, Burrell R. Acute phase reactants in experimental inhalation lung disease. Proc. Soc. Exp. Biol. 111, 49–55 (1981).

Baseler M W, Burrell R. Purification of haptoglobin and its effects on lymphocyte and alveolar macrophage responses. Inflamm. 7, 387–400 (1983).

Oh S K, Kim S U, Walker J E. Interference with immune response at the level of generating effector cells by tumor-associated haptoglobin. J. Natl. Canc. Inst. 82, 934–40 (1990).

Oh S K, Very D L, Walker J, Raam 5, Ju S T. An analogy between fetal haptoglobin and a potent immunosuppressant in cancer. Cancer Res. 47, 5120–6 (1987).

El Ghmati S M, Van Hoeyveld E M, Van Strijp A G, Ceuppens J L, Stevens E A M. Identification of haptoglobin as an alternative ligand for CD1 lb/CD 18. J. Immunol. 156, 2542–52 (1996).

van Dijk, W., Turner G. A., Mackiewicz, A. Changes in glycosylation of acute-phase proteins in health and disease: occurrence, regulation and function. Glycosy/. Dis. 1, 5–14 (1994).

van Dijk, W. and Mackiewicz, A. Interleukin-6-type cytokine-induced changes in acute phase protein glycosylation. Ann. NY Acad. Set 762, 319–330 (1995).

Sharpe-Timms, K. L., Piva, M., Ricke, E. A. Extrahepatic vs. hepatic haptoglobin in women with endometriosis. Soc. Gynecol. Invest. Chicago, Ill. Abstract 825 (2000).

Tseng, J. F., Ryan I. P., Milam T. D., Murai J. T., Schriock E. D., Landers D. V., and Taylor R. N. Interleukin-6 secretion in vitro is up-regulated in ectopic and eutopic endometrial stromal cells from women with endometriosis. J. C/in. Endocrinol. Metab. 81, 1118–1122 (1996).

Dobryszycka W. Biological Functions of haptoglobin-new pieces to an old puzzle. Euro. J. C/in. Chem. C/in. Biochem. 35, 647–54 (1997).

Langlois M R, Delanghe J R. Biological and clinical significance of haptoglobin polymorphism in humans. C/in. Chem. 42,1589–1600 (1996).

Thorton, B. P., Vetvicka, V., Pitman, M., Goldman, R. C., Ross, G. D. Analysis of the sugar specificity and molecular location of the beta-glucan binding lectin site of complement receptor type 3 (CD11b/CD18). J Immuno/. 156:1235–46 (1996).

Ualme, J., Becker, S., Uaskill, S. Altered maturation and function of peritoneal macrophages: possible pathogenesis of endometriosis. Am. J. Obstet. Gyneco/. 156:783–9 (1987).

van der Straten, A., Uerzog, A., Cabezon, T., Bollen, A. Characterization of human haptoglobin cDNAs coding for alpha 2FS beta and alpha iS beta variants, FEBS Lett. 168, 103–107 (1984).

Piva, M., Horowitz G., and Sharpe-Timms, K. Human peritoneal endometriotic lesions express all three haptoglobin cx-chain phenotypes. *Biol. Reprod.* 60. Suppl. 1, 261 (1999).

Brinkman-van der Linden, C. M., de Uaan, P. F., Uavenaar, E, C, and van Dijk, W. Inflammation-induced expression of sialyl Lewis-X is not restricted to alphal-acid glycoprotein but also occurs to a lesser extent on alphal-antichymotrypsin and haptoglobin. *G/ycoconjJ.* 15, 177–82 (1998).

Knibbs, R. N., Goldstein, I. J., Ratcliffe, R. M., and Shibuya N. Characterization of the carbohydrate binding specificity of the leukoagglutinating lectin from *Maackia amurensis*. *J Bio/. Chem.* 266, 83–88 (1991).

Goodarzi, M. T., Turner, G. A. A lectin method for investigating the glycosylation of nanogram amounts of purified glycoprotein. *Glycoconj. J.* 14, 493–496 (1997).

Yan, L., Wilkins, P.P., Alvarez-Manilla, G., Do, S. J., Smith, D. F., and Cummings R D. Immobilized Lotus tetragonolobus agglutinin binds oligosaccharides containing the Le(x) determinant. *G/ycoconj. J.* 14, 45–55 (1997).

Debray, U., Decout, D., Strecker, G., Spik, G., Montreuil, J. Specificity of twelve lectins towards oligosaccharides and glycopeptides related to N-Glycosyl proteins. *Eur. J. Biochem.* 117, 41–55 (1981).

Osteen K G, Hill G A, Hargrove J T, Gorstein F. Development of a method to isolate and culture highly purified populations of stromal and epithelial cells from human endometrial biopsy specimens. *Fertil. Steril.* 52, 965–72 (1989).

Maeda, N. DNA polymorphisms in the controlling region of the human haptoglobin genes: a molecular explanation for the haptoglobin 2–1 modified phenotype. *Am. J. Hum. Genet.* 49, 158–166 (1991).

Ferens-Sieczkowska M. Midro A., Mierzejewska-Iwanowska B., Zwierz K., Katnik-Prastowska I. Uaptoglobin glycoforms in a case of carbohydrate-deficient glycoprotein syndrome, *Glycoconj. J.* 16, 573–577 (1999).

Ferens-Sieczkowska, M. and Olczak, M. Carbohydrate structures of haptoglobin in sera of healthy people and a patient with congenital disorder of glycosylation. *Z Naturforsch.* 56,122-b 1 (2001).

Goodarzi, M. T., Turner G. A. Reproducible and sensitive determination of charged oligosaccharides from haptoglobin by PNGase F digestion and UPAEC/PAD analysis: glycan composition varies with disease, *Glycoconj. J.* 15, 469–475 (1998).

Nemansky, M., Schiphorst, W. E. C. M., and Van der Eijnden, D. U. Branching and elongation with lactosaminoglycan chains of N-linked oligosaccharides result in a shift toward termination with α2>3-linked rather than α2>6-linked sialic acid residues. *FEBS Lett.* 363, 280–284 (1995).

Turner G A., Goodarzi, M. T., and Thompson, S. Glycosylation of alpha-1-proteinase inhibitor and haptoglobin in ovarian cancer: evidence for two different mechanisms. *Glycoconj. J* 12, 211–218 (1995).

Thompson, S., Cantwell, B. M., Matta, K. L., and Turner, G. A. Parallel changes in the blood levels of abnormally-fucosylated haptoglobin and alpha 1,3 fucosyltransferase in relationship to tumour burden: more evidence for a disturbance of fucose metabolism in cancer. *Cancer Lett* 65, 115–121 (1992).

de Graaf, T. W., Van der Stelt, M. E., Anbergen, M. G., van Dijk W. Inflammation-induced expression of sialyl Lewis X-containing glycan structures on cu-acid glycoprotein (orosomucoid) in human sera. *J. Exp. Med.* 177, 657–666 (1993).

Mann, A. C., Record, C. O., Self, C. U., Turner, G. A. Monosaccharide composition of haptoglobin in liver diseases and alcohol abuse: large changes in glycosylation associated with alcoholic liver disease, *C/in. Chim. Acta* 227, 69–78 (1994).

Dunselman, G. A., Bouckaert, P. X., Evers, J. L. The acute phase response in endometriosis of women. J. Reprod. Fertil. 83:803–8 (1988).

Hanley, J. M., Haugen, T. H., and Heath, E. C. Biosynthesis and processing of rat haptoglobin. *J. Biol. Chem.* 258, 7858–7869 (1983).

Montreuil, J. Recombinant glycoproteins: pitfalls and strategy, in: S. Dumitriu, (ed.). Polysaccharides in medical applications. *Marcel Dekker*, New York, N.Y., pp. 481–490 (1996).

Raju, T. S., Stanley, P. Gain-of-function Chinese hamster ovary mutants LEC18 and LEC 14 each express a novel N-acetylglucosaminyltransferase activity. J. Biol. Chem. 273:14090–8 (1998).

Rothlein, R., Springer, T. A. Complement receptor type three-dependent degradation of opsonized erythrocytes by mouse macrophages. *JImmunol* b5:2668–72 (1985).

Ding, A., Wright, S. W., Nathan, C. Activation of murine macrophages by monoclonal antibodies to Mac-i (complement receptor type 3). *JExper Med* 165:733–49 (1987).

Oh, S. K., Ross, S., Walker, J. M., Zeisel, S. Role of a SER immune suppressor in immune surveillance. *Immunology* 64:73–9 (1988).

Yong, K., Khwaja, A. Leukocyte cellular adhesion molecules. *Blood Reviews* 4:211–25 (1990).

Fan, S. T., Edgington, T. S. Integrin regulation of leukocyte inflammatory functions. *J Immunol* 150:2972–80 (1993).

What is claimed is:

1. A method of diagnosing endometriosis in a female patient suspected of having endometriosis by:
   (a) obtaining an endometrial tissue sample from the patient; and
   (b) detecting an increased level of an endometriotic haptoglobin in the sample from the patient, wherein the endometriotic haptoglobin is a haptoglobin designated ENDO-I secreted from endometrial and/or endometriotic tissue and having a molecular weight of between 35,000 and 55,000 Da at an isoelectric point of 4.0 to 5.5 as determined by 2-dimensional sodium dodecyl sulfate polyacrylamide gel electrophoresis (2-D SDS-PAGE), as compared to the level of the endometriotic haptoglobin detected in an endometrial tissue sample of a female patient without endometriosis as indicative of endometriosis in the patient, wherein the detecting is performed with a method selected from immunohistochemical staining of the sample or immunoassay of secretions from the sample after in vitro incubation.

2. The method of claim 1 wherein the detecting is performed by immunohistochemical staining of the sample.

3. The method of claim 2 wherein the staining is performed with an antibody specific for the endometriotic haptoglobin designated ENDO-I.

* * * * *

SEQUENCE LISTING

<160> NUMBER OF SEQ ID NOS: 16

<210> SEQ ID NO 1
<211> LENGTH: 855
<212> TYPE: DNA
<213> ORGANISM: Homo sapien

<400> SEQUENCE: 1

-continued

```
taagatggtt tcccaccata atctccaccac aggtgccacg ctgatcaatg aacaatggct        60
gctgaccacg gctaaaaatc tcttcctgaa ccattccaca aatgcaacag cgaaagacat       120
tgcccctact ttaacactct atgtggggaa aaagcacctt gtagagattg aaaaggttgt       180
tctacacccc aactactccc agtagatat tgggctcatc aaactcaaac agaaggtgtc        240
tgttaatgag agagtgatgc ccatctgcct accttcaaag gattatgcag aagtagggcg       300
tgtgggttat gtttctggct ggggggcgaaa tgccaatttt aaatttactg accatctgaa      360
gtatgtcatg ctgcctgtgg ctgaccaaga ccaatgcata aggcattatg aaggcagcac       420
agtccccgaa aagaagacac cgaagagccc tgtaggggtg cagcccatac tgaatgaaca       480
caccttctgt gctggcatgt ctaagtacca agaagacacc tgctatggcg atgcgggcag      540
tgcctttgcc gttcacgacc tggaggagga cacctggtat cgactgggga tcttaagctt      600
tgataagagc tgtgctgtgg ctgagtatgg tgtgtatgtg aaggtgactt ccatccagga      660
ctgggttcag aagaccatag ctgagaacta atgcaaggct ggccggaagc ccttgcctga      720
aagcaagatt tcaacctgga gagggcaaa gtggacggga gtggacagga gtggatgcga       780
taagatgtgg tttgaacctg atgggtgcca gccctgcatt gctgagtcaa tcaataaaga       840
gctttctttt gaccc                                                         855
```

```
<210> SEQ ID NO 2
<211> LENGTH: 859
<212> TYPE: DNA
<213> ORGANISM: Homo sapien

<400> SEQUENCE: 2
```

```
gacgccaaag gcagctttcc ttggcaggcc aagatgatct ccagacatgg actcaccact        60
ggggccacac tgatcagtga ccagtggctg ctgaccactg cccaaaacct cttcctgaat       120
cacagtgaga atgcgacagc caaggacatt gccccctacctt aacactcta tgtggggaaa     180 aaccagctgg tggagattga gaaggtagtt ctccaccccg agcgctctgt ggtggatatc       240
gggctgatca agctcaaaca gaaagtgctt gtcactgaga aagtcatgcc tatctgcctg       300
ccttccaaag actacgtagc gccaggccgc atgggctatg tgtccggttg ggggcggaat      360
gtcaacttta gatttactga acgtctcaag tatgtcatgc tgcctgtggc tgaccaggag      420
aagtgtgagc tgcactatga gaaaagcaca gtgcctgaga agaaaggcgc tgtaagtcct      480 gttgggtac agcccatctt gaataagcat accttctgtg ctggccttac caagtatgag       540
gaagacactt gctatggtga cgctggcagt gcctttgccg tccatgacac ggaggaggac     600
acctggtatg cagctgggat cctgagcttt gacaagagtt gtgccgtagc tgagtatggt     660
gtgtacgtga gggcaactga tctgaaggac tgggtccagg aaacaatggc caagaactag      720
ttcagggctg actagagggc tgcacacagt ggggcagggc aattcaccct ggaagaggaa      780
gtagaagggt tggggacata atctgagggc tgctagccct gcattgctca gtcaataata      840
aaaaacgagc tttggaccc                                                    859
```

```
<210> SEQ ID NO 3
<211> LENGTH: 19
<212> TYPE: PRT
<213> ORGANISM: Homo sapien

<400> SEQUENCE: 3

Ile Ile Gly Gly Ser Met Asp Ala Lys Gly Ser Phe Pro Cys Gln Ala
1               5                   10                  15
```

Thr Asn Cys

<210> SEQ ID NO 4
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: primer

<400> SEQUENCE: 4
gacgccaaag gcagctttcc ttggcaggcc             30

<210> SEQ ID NO 5
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: forward primer

<400> SEQUENCE: 5
ccacccatgg caaattccat ggca                   24

<210> SEQ ID NO 6
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: reverse primer

<400> SEQUENCE: 6
gctaagcagt tggtggtgca gga                    23

<210> SEQ ID NO 7
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: primer

<400> SEQUENCE: 7
ctcaagtatg tcatgctgcc                        20

<210> SEQ ID NO 8
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: primer

<400> SEQUENCE: 8

```
actaccttct caatctccac cagc                                          24

<210> SEQ ID NO 9
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: forward primer for humans

<400> SEQUENCE: 9
gatgccaaag gcagctttcc ctggcaggct                                    30

<210> SEQ ID NO 10
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: reverse primer for humans

<400> SEQUENCE: 10
cacacacagg ccacgcgtcg actagtac                                      28

<210> SEQ ID NO 11
<211> LENGTH: 250
<212> TYPE: DNA
<213> ORGANISM: Artificial sequence
<220> FEATURE:
<223> OTHER INFORMATION: Probe
<220> FEATURE:
<221> NAME/KEY: misc_feature
<222> LOCATION: (1)..(250)
<223> OTHER INFORMATION: probe for human ENDO-I

<400> SEQUENCE: 11
ttcccaccat aatctcacca caggtgccac gctgatcaat gaacaatggc tgctgaccac    60
ggctaaaaat ctcttcctga accattcaca aaatgcaaca gcgaaagaca ttgccctac   120 tttaacactc tatgtgggga aaaagcacct tgtagagatt gaaaaggttg ttctacaccc   180
caactactcc caggtagata ttgggctcat caaactcaaa cagaaggtgt ctgttaatga   240
gagagtgatg                                                         250

<210> SEQ ID NO 12
<211> LENGTH: 50
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(50)
<223> OTHER INFORMATION: synthesis primer

<400> SEQUENCE: 12
ttctagaatt cagcggccgc tttttttttt tttttttttt tttttttttt              50

<210> SEQ ID NO 13
<211> LENGTH: 34
<212> TYPE: DNA
```

```
-continued

<213> ORGANISM: Artificial sequence
<220> FEATURE:
<223> OTHER INFORMATION: Primer
<220> FEATURE:
<221> NAME/KEY: misc_feature
<222> LOCATION: (1)..(34)
<223> OTHER INFORMATION: forward primer

<400> SEQUENCE: 13
gggaattcag aggcaagacc aaccaagatg agtg                          34

<210> SEQ ID NO 14
<211> LENGTH: 46
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(46)
<223> OTHER INFORMATION: reverse primer

<400> SEQUENCE: 14
gtctagactt atcgtcatcg tcgttctcag ctatggtctt ctgccc             46

<210> SEQ ID NO 15
<211> LENGTH: 4
<212> TYPE: PRT
<213> ORGANISM: Artificial sequence
<220> FEATURE:
<223> OTHER INFORMATION: Endonuclease cleavage site
<220> FEATURE:
<221> NAME/KEY: SITE
<222> LOCATION: (1)..(4)
<223> OTHER INFORMATION: endonuclease cleavage site

<400> SEQUENCE: 15

Asp Asp Asp Lys
1

<210> SEQ ID NO 16
<211> LENGTH: 14
<212> TYPE: PRT
<213> ORGANISM: Artificial sequence
<220> FEATURE:
<223> OTHER INFORMATION: Epitope
<220> FEATURE:
<221> NAME/KEY: MISC_FEATURE
<222> LOCATION: (1)..(14)
<223> OTHER INFORMATION: VS epitope

<400> SEQUENCE: 16

Gly Lys Pro Ile Pro Asn Pro Leu Leu Gly Leu Asp Ser Thr
1               5                   10
```